United States Patent [19]
Nishihara et al.

[11] Patent Number: 5,272,625
[45] Date of Patent: Dec. 21, 1993

[54] MEDICAL IMAGE DATA MANAGING SYSTEM

[75] Inventors: Eitaro Nishihara, Ootwara; Yuki Fukushima, Tochigi; Takehiro Ema, Ootwara, all of Japan

[73] Assignee: Kabushiki Kaisha Toshiba, Kawasaki, Japan

[21] Appl. No.: 701,517

[22] Filed: May 16, 1991

[30] Foreign Application Priority Data
May 17, 1990 [JP] Japan .................................. 2-125331
Jul. 19, 1990 [JP] Japan .................................. 2-191948

[51] Int. Cl.⁵ .............................................. G06F 15/00
[52] U.S. Cl. ................................................ 364/413.13
[58] Field of Search ...................... 364/413.13, 413.01, 364/413.14

[56] References Cited
U.S. PATENT DOCUMENTS
4,958,283 9/1990 Tawara et al. .................. 364/413.13

Primary Examiner—Roy N. Envall, Jr.
Assistant Examiner—Ari H. Bai
Attorney, Agent, or Firm—Oblon, Spivak, McClelland, Maier & Neustadt

[57] ABSTRACT

In a medical image data managing system, a directory managing unit is employed so as to manage directory data on overall medical image data. The medical image data managing system comprises: a plurality of modality units for producing medical image data in accordance with sorts of the modality unit a plurality of database units for storing at least the medical image data produced from the modality units: workstation units for issuing a demand to fetch desirable medical image data from the database units and for displaying the fetched medical image data; and, a directory managing unit for storing directory information about to which database units the desirable medical image data has been stored and for outputting the directory information upon receipt of the demand issued from the workstation means.

6 Claims, 25 Drawing Sheets

| PATIENT NO. | PATIENT NAME | SEX | BIRTH DATA | DIAGNOSTIC DEPT. | EXAMINATION NAME | EXAMINATION DATE | STORAGE ADDRESS | |
|---|---|---|---|---|---|---|---|---|
| | | | | | | | ADDRESS | DB-NO. |
| 01 | SATO | M | 1900-5-15 | SURGERY | CT | 91'-2-14 | 1 | 01 |
| 02 | KATO | M | 1920-3-15 | INT. MEDICINE | XR | 91'-2-14 | 2 | 01 |
| 03 | ODA | M | 1930-2-25 | INT. MEDICINE | CT | 91'-2-15 | 2 | 02 |
| 04 | KINOSHITA | M | 1930-7-12 | INT. MEDICINE | XR | 91'-2-15 | 2 | 03 |
| 05 | AKECHI | M | 1920-4-30 | SURGERY | CT | 91'-2-16 | 1 | 02 |
| 06 | SAITO | F | 1940-3-12 | OBSTETRICS | US | 91'-2-16 | 3 | 01 |
| ...... | ...... | ...... | ...... | ...... | ...... | ...... | ...... | ...... |

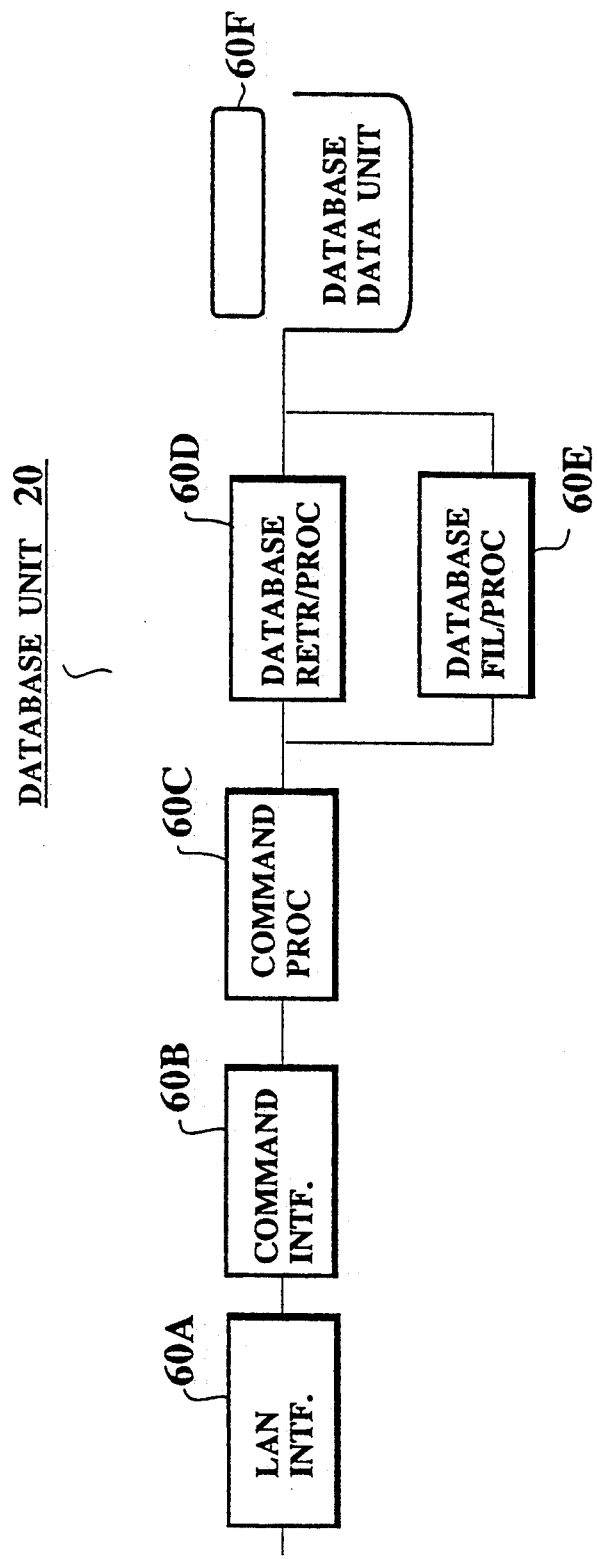

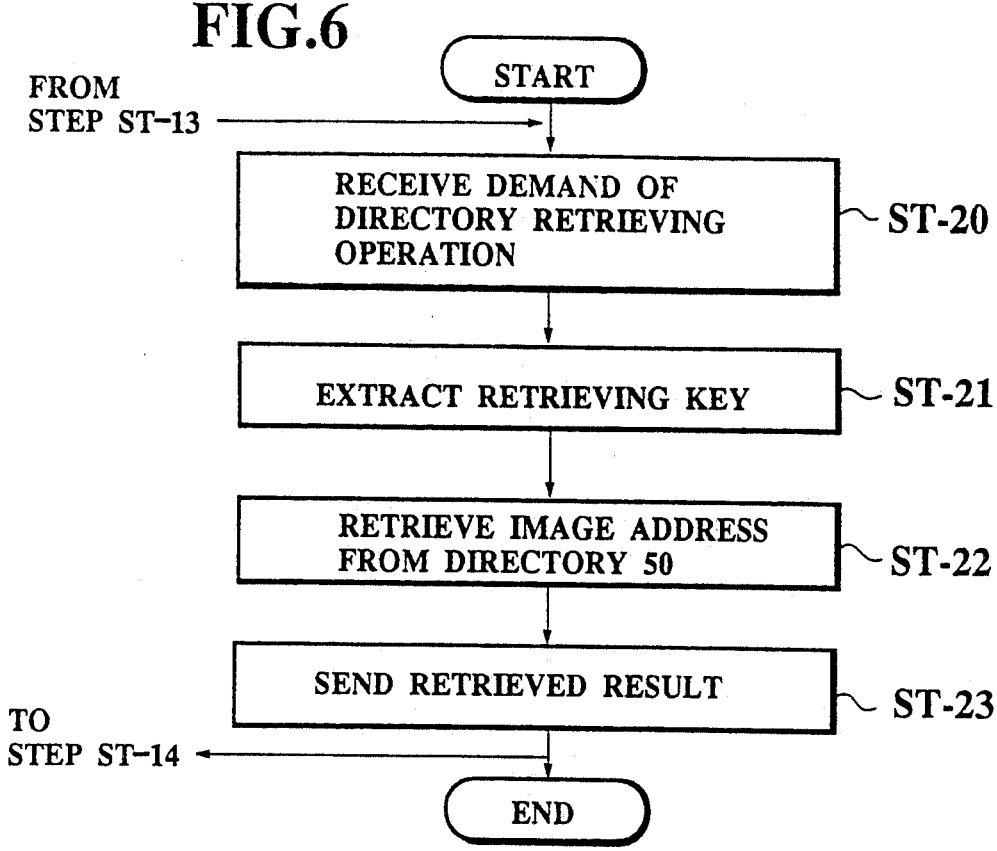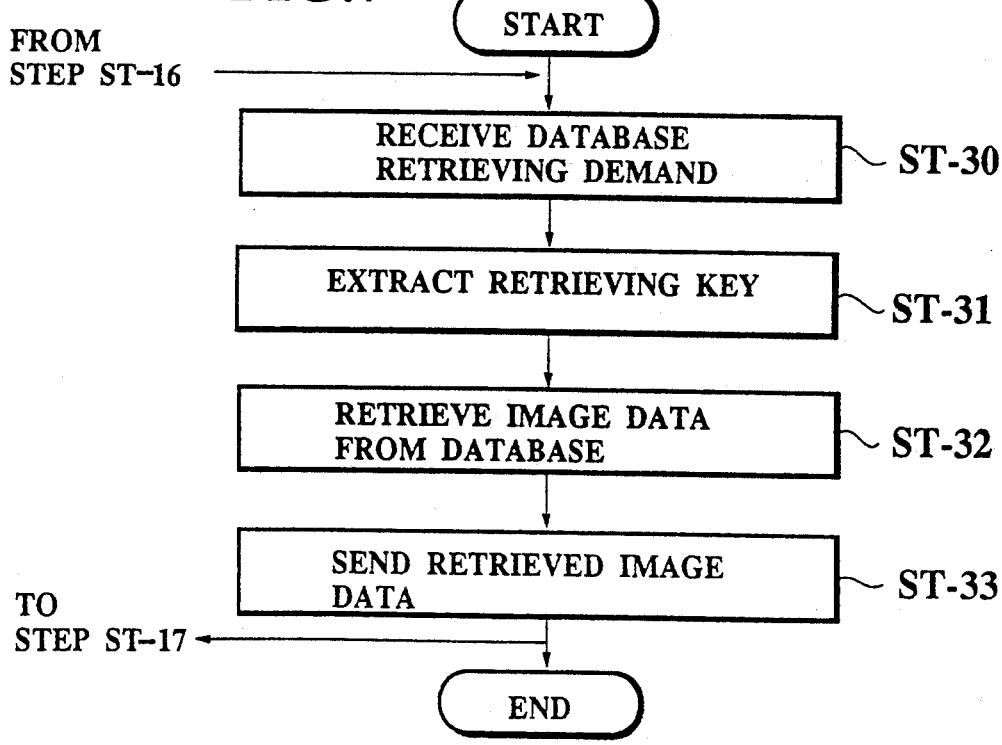

FIG.16

| PATIENT ID | EXAMINATION ID | NAME OF DATABASE | EXAMINATION IMAGE VOLUME |
|---|---|---|---|
| P00001 | E00105 | DATABASE-1 | 2 MB |
| P00001 | E00143 | DATABASE-3 | 5 MB |
| P00001 | E00210 | DATABASE-2 | 18 MB |
| P00003 | E00008 | DATABASE-2 | 5 MB |
| P00010 | E00276 | DATABASE-1 | 15 MB |
| .... | .... | .... | .... |

FIG.17

| PATIENT NO. | PATIENT NAME | SEX | BIRTH | DIAGNOSTIC DEPT | DIAGNOSIS | EXAMINATION DATE | STORAGE ADDRESS | |
|---|---|---|---|---|---|---|---|---|
| | | | | | | | DB-NO. | ADDRESS |
| 01 | SATO | M | 1900-5-15 | SURGERY | CT | 91'-2-14 | 1 | 01 |
| 05 | AKECHI | M | 1920-4-30 | SURGERY | CT | 91'-2-16 | 1 | 02 |
| 07 | SANADA | M | 1990-2-10 | SURGERY | XR | 91'-2-16 | 1 | 03 |
| .... | .... | .... | .... | .... | .... | .... | .... | .... |

FIG.18

| PATIENT NO. | PATIENT NAME | SEX | BIRTH | DIAGNOSTIC DEPT. | DIAGNOSIS | EXAMINATION DATE | STORAGE ADDRESS | |
|---|---|---|---|---|---|---|---|---|
| | | | | | | | DB-NO. | ADDRESS |
| 02 | KATO | M | 1920-3-12 | INT. MEDICINE | XR | 91'-2-14 | 2 | 01 |
| 03 | ODA | M | 1930-2-25 | INT. MEDICINE | CT | 91'-2-15 | 2 | 02 |
| 04 | KINOSHITA | M | 1945-7-12 | INT. MEDICINE | XR | 91'-2-15 | 2 | 03 |
| ..... | ..... | ..... | ..... | ..... | ..... | ..... | ..... | ..... |

FIG.19

| PATIENT NO. | PATIENT NAME | SEX | BIRTH | DIAGNOSTIC DEPT. | DIAGNOSIS | EXAMINATION DATE | STORAGE ADDRESS | |
|---|---|---|---|---|---|---|---|---|
| | | | | | | | DB-NO. | ADDRESS |
| 06 | SATO | F | 1942-3-12 | OBSTETRICS | US | 91'-2-16 | 3 | 01 |
| ..... | ..... | ..... | ..... | ..... | ..... | ..... | ..... | ..... |

| NAME OF EXAM. APPR. | DATABASE |
|---|---|
| CT | DATABASE-1 |
| MRI | DATABASE-2 |
| X-RAY | DATABASE-3 |
| X-RAY | DATABASE-4 |

FIG.26

| DIAGNOSTIC DEPT | FILING DESTINATION |
|---|---|
| INT. MED. | FILING APP-A |
| SURG. | FILING APP-B |
| PED. | FILING APP-C |
| BRA. SURG | FILING APP-D |
| ⋮ | ⋮ |

FIG.27A

```
SELECT BASIS TO CATEGORIZE DATABASE
              JUDGING SEQUENCE
PATIENT ID         _____
EXA. ID               2
DIAG. DEPT.        _____
NAME OF MODALITY      1
MODALITY ID        _____

PRESS ESC-KEY UPON END OF INPUT OPERATION
```

FIG.27B

```
INPUT RELATIONSHIP BETWEEN MODALITY
AND RELEVANT DATABASE

NAME OF MODALITY        DATABASE

MRI                DATABASE-1 ■

_____              _____

_____              _____

_____              _____

PRESS ESC-KEY UPON END OF INPUT OPERATION
```

FIG.27C

```
INPUT RELATIONSHIP BETWEEN
PATIENT ID AND RELEVANT DATABASE

PATIENT ID              DATABASE

1~99                DATABASE-2

100~199              DATA ■

200~299              _____

300~399              _____

PRESS ESC-KEY UPON END OF INPUT OPERATION
```

FIG.27D

```
FILING DESTINATION INFORMATION
IS GIVEN AS:

KEY                      DATABASE

NAME OF MODALITY MRI         DATABASE-1

PATIENT ID    1~99         DATABASE-2

PATIENT ID   100~199       DATABASE-3

PATIENT ID   200~299       DATABASE-4

PRESS F1-KEY IF OK, F9-KEY IF NOT
```

FIG.28

| NAME OF MODALITY | DATABASE |
|---|---|
| MRI | DATABASE-1 |

| PATIENT ID | DATABASE |
|---|---|
| 1~99 | DATABASE-2 |
| 100~199 | DATABASE-3 |
| 200~299 | DATABASE-4 |
| ⋮ | ⋮ |

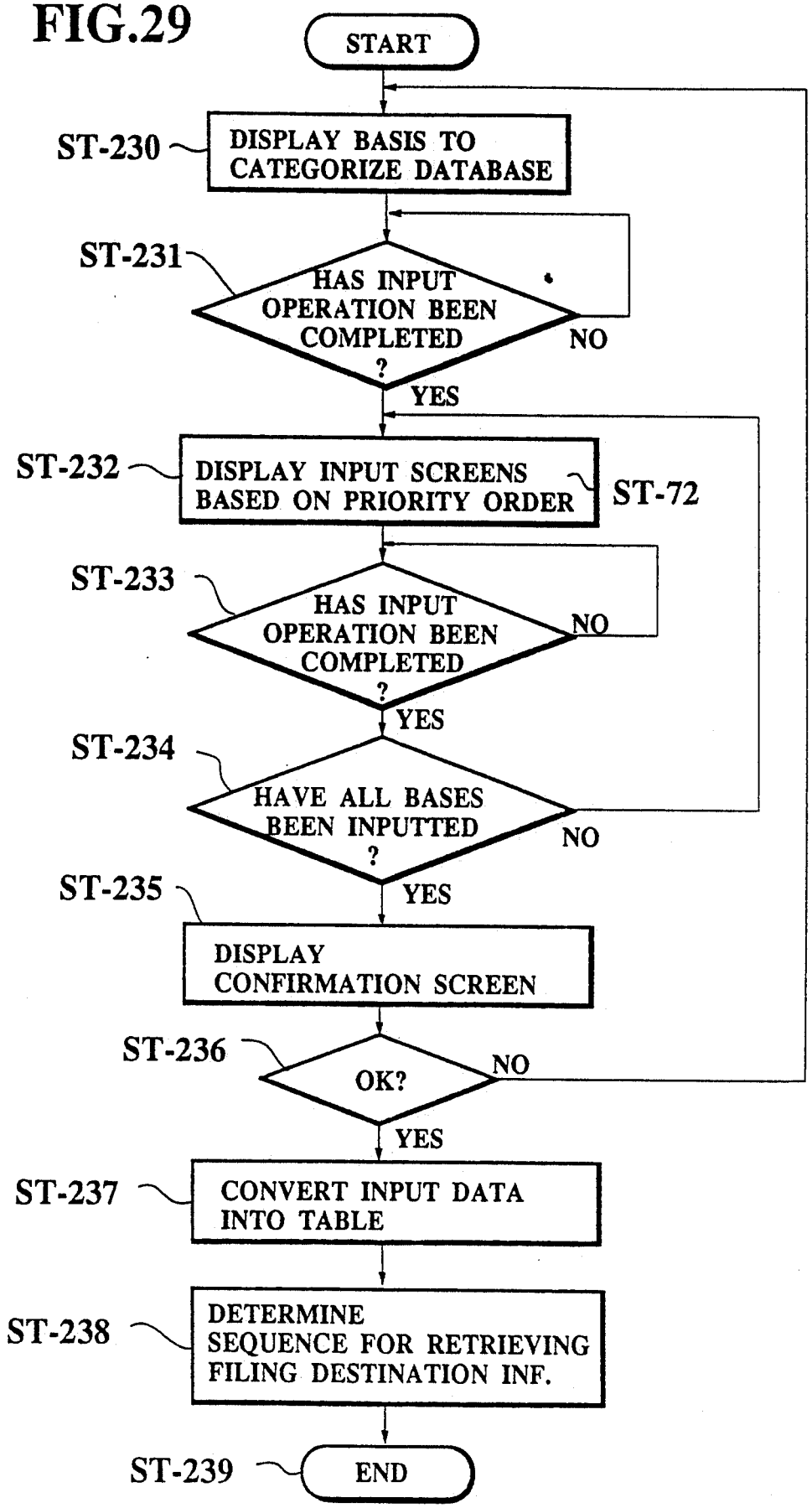

FIG.31A
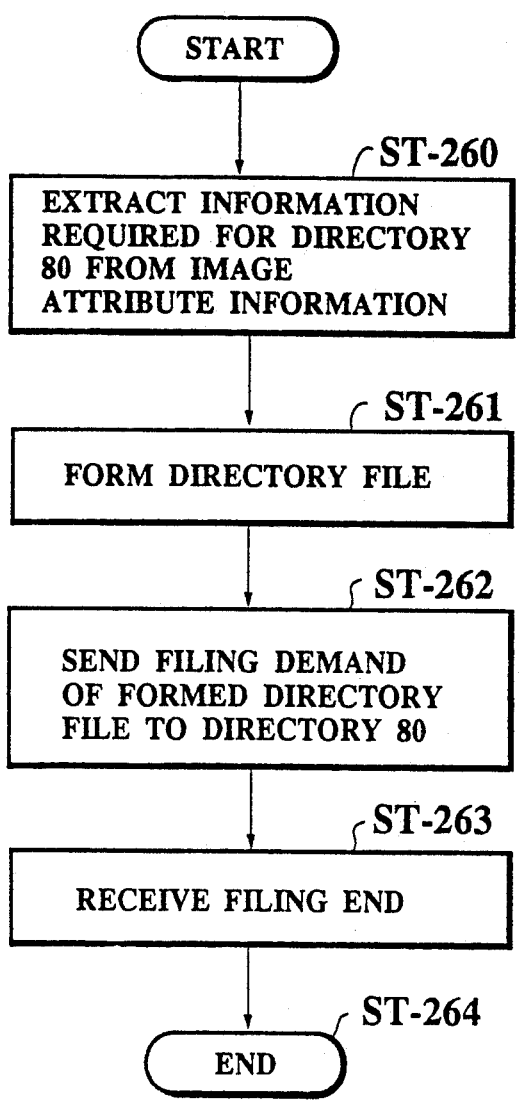
FIG.31B
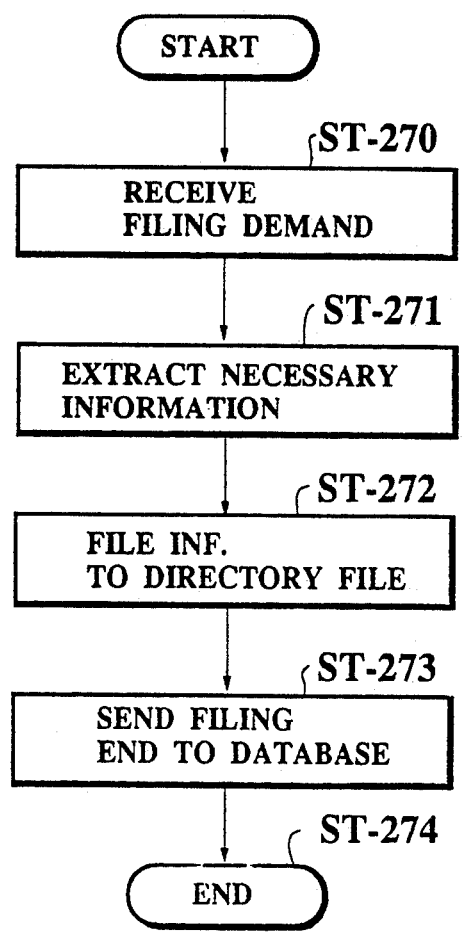
FIG.32
| DIAGNOSTIC DEPT | DATABASE |
|---|---|
| INF. MED. | DATABASE-1 |
| SURG. | DATABASE-2 |
| PED. | DATABASE-3 |
| ⋮ | ⋮ |

MEDICAL IMAGE DATA MANAGING SYSTEM

BACKGROUND OF THE INVENTION

1. Field of the Invention

The present invention generally relates to a medical image data managing system. More specifically, the present invention is directed to an image data retrieving system for a distributed type image data base and also a medical image data filing system.

2. Description of the Related Art

In a conventional distributed type medical image data managing system, there are plural databases into which the medical image data obtained from the various modalities such as X-ray CT apparatus, MRI apparatus and ultrasonic imaging apparatus, together with attribute information thereof have been stored. In such a conventional data managing system, one database manages only own image data stored therein. If other image data stored in other databases are required to be retrieved, lengthy and cumbersome data retrieving operations are necessarily carried out.

That is, a plurality of retrieval demands must be sent to the various databases until the image data which is required by a user can be found out. Since such retrieval demands or interrogations are simultaneously transmitted to not only the relevant database actually having the desirable image data but also other databases, the resultant response time is unwantedly prolonged.

On the other hand, in a conventional medical image data filing system, the contents of diagnosis become further complex and the diagnostic ranges are widened. To accept such developments of the medical services, the filing formats must be varied from time to time. In this case, the filing destination information related to the respective medical image generating apparatuses, namely modalities such as X-ray CT apparatuses and MRI apparatuses must be changed in each of these modalities. This may cause very cumbersome works in order to change the filing destination information.

SUMMARY OF THE INVENTION

The present invention has been made in an attempt to solve the above-described problems of both the conventional medical image data managing system and also medical image data filing system, and therefore has an object to provide a simple image data managing system and also an image data filing system capable of easily changing destination information on filing work.

A medical image data managing system, according to the present invention, comprises:

a plurality of modality units (10:14) for producing medical image data in accordance with sorts of the modality unit (10:14);

a plurality of database units (20:24) for storing at least said medical image data produced from said modality units (10:14);

workstation means (30:32) for issuing a demand to fetch desirable medical image data from said database units (20:24) and for displaying the fetched medical image data; and, directory managing means (50) for storing directory information about to which database units said desirable medical image data has been stored and for outputting said directory information upon receipt of said demand issued from said workstation means (30:32).

Furthermore, another medical image data managing system, according to the present invention, comprises:

a plurality of modality units (10:14) for producing medical image data in accordance with sorts of the modality units (10:14);

a plurality of database units (20:24) for storing at least said medical image data produced from said modality units (10:14);

storage means (80) including a file for storing data filing destination information about a relationship between said medical image data and attribute data thereof; and, workstation means (30:32) for issuing a demand to file the medical image data produced from said modality units (10:14) into said database units (20:24) by transferring said demand to the storage means (80) so as to obtain said data filing destination information from said file.

BRIEF DESCRIPTION OF THE DRAWINGS

For a better understanding of the above object of the present invention, reference is made to the following detailed description of the invention to be read in conjunction with the following drawings, in which:

FIG. 4B is a schematic block diagram of an internal arrangement of the database unit 20;

FIG. 5 to 7 are flowcharts for explaining a first image data retrieving operation effected in the system 100;

FIGS. 16 to 19 represent contents of directory files employed in the third image data retrieving method;

FIG. 26 represents a content of a first filing destination information file;

FIGS. 27A to 27D represent input screens during the first data filing operation;

FIG. 28 represents a content of a second filing destination information file;

FIG. 29 is a flowchart for explaining the filing destination information filing operation effected in the storage unit 80;

FIGS. 31A and 31B are flowcharts for explaining a third directory filing operation executed in the system 200; and, FIG. 32 represents a content of a directory file used in the third directory filing operation.

DETAILED DESCRIPTION OF THE PREFERRED EMBODIMENTS

As previously described, an image data retrieving system is one of the major features according to the present invention.

Figures 1, 2:
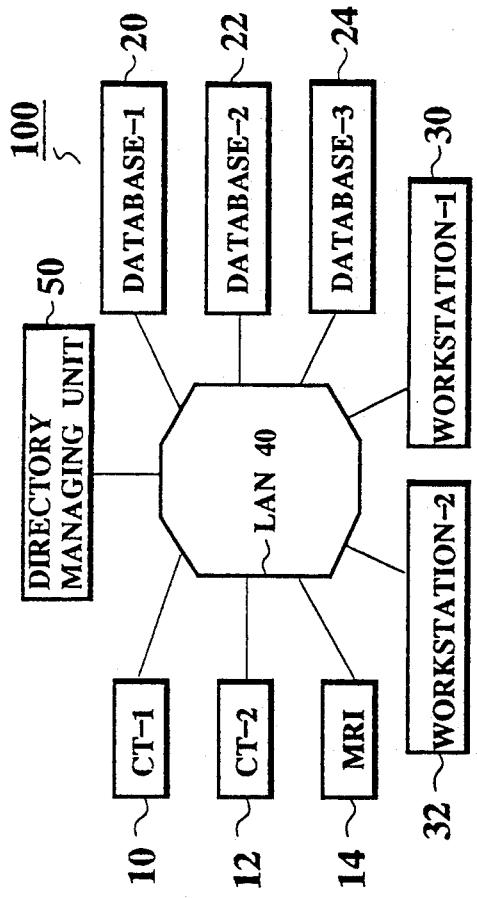
FIG. 1 is a schematic block diagram for showing an overall medical image data managing system according to a first preferred embodiment of the present invention.
FIG. 2 represents a content of a directory file stored in the directory managing unit 50 employed in the system 100 shown in FIG. 1.

FIG. 1 represents an overall image data retrieving system 100 according to a first preferred embodiment.

In the first image data retrieving system 100 shown in FIG. 1, a plurality of modalities such as X-ray CT apparatuses 10, 12 and MRI apparatus 14 are employed to produce various medical image data. Also, a plurality of database units 20, 22, 24 are employed to store therein the preselected medical image data produced by the respective modalities 10 to 14. A first workstation 30 and a second workstation 32 are provided to mainly perform various data processing operations and data retrieving operation. A directory managing unit 50 is coupled via a local area network (referred to as a "LAN") 40 to all of the above-described system components 10-14, 20-24, 30 and 32. The directory managing unit 50 stores therein information about to which database unit, the retrieving image data has been stored (will be discussed more in detail). This directory managing unit 50 includes a directory file as represented in FIG. 2. As shown in this directory file, various medical data on patients and the data storage information have been previously stored.

Figure 3:
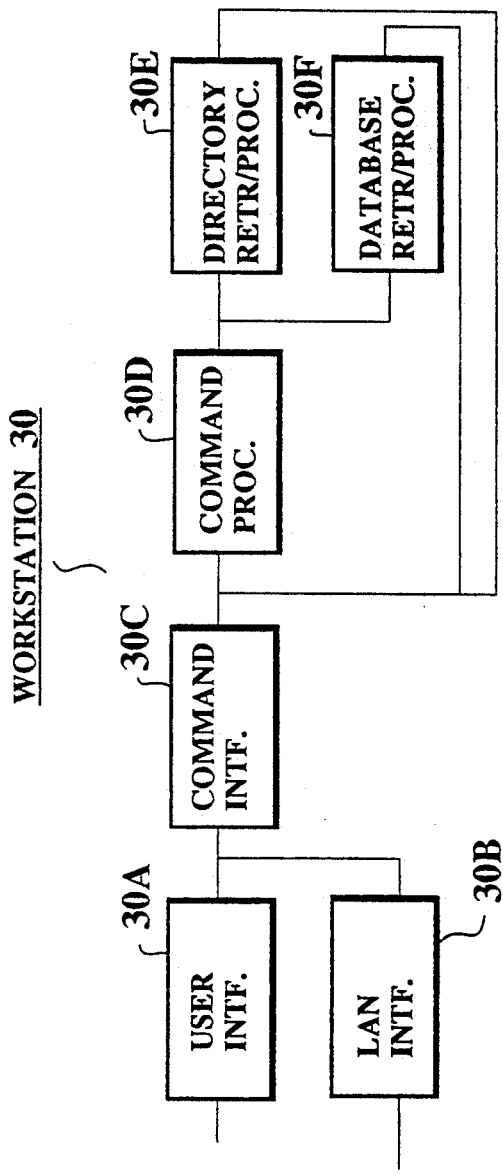
FIG. 3 is a schematic block diagram of an internal arrangement of the workstation 30 employed in the first system 100 shown in FIG. 1.

FIG. 3 illustrates an internal arrangement of the first workstation 30. In the workstation 30, a user interface unit 30A and a LAN interface unit 30B are connected to a user's device (not shown) and LAN 40. Furthermore, a command interface unit 30C, a command processing unit 30D, a directory retrieving/processing unit 30E and a database retrieving/processing unit 30F (detailed operations will be described).

Figure 4A:
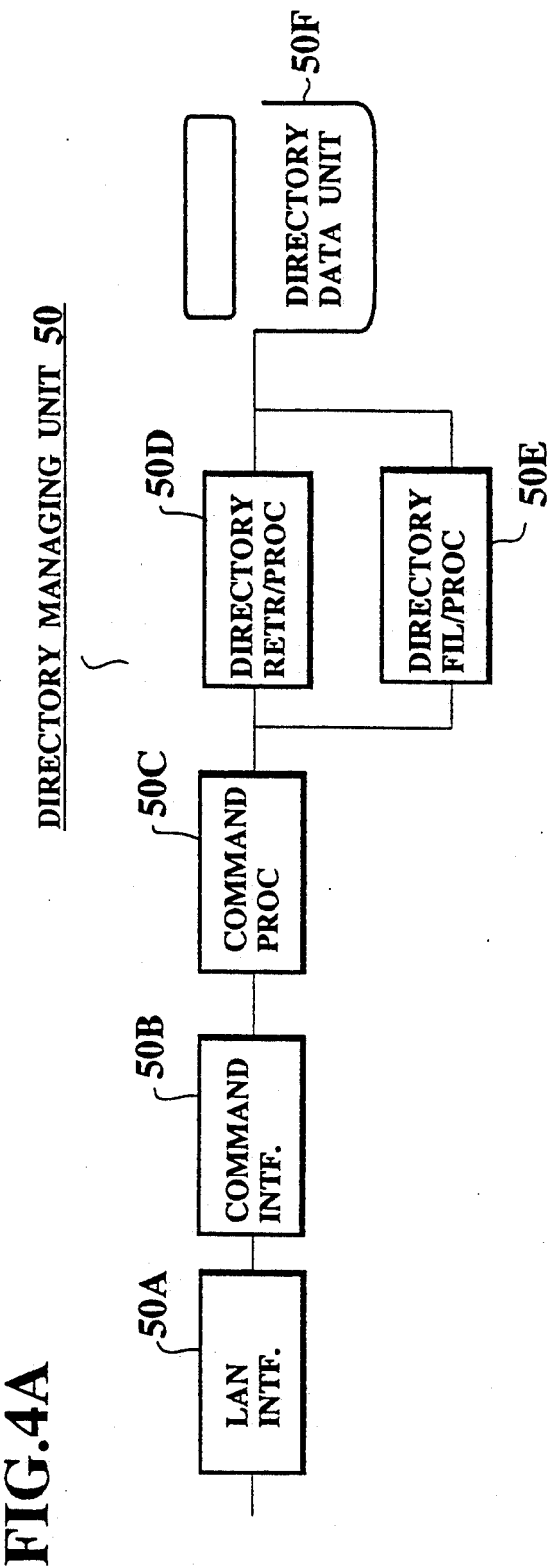
FIG. 4A is a schematic block diagram of an internal arrangement of the directory managing unit 50.

FIG. 4A represents an internal arrangement of the directory managing unit 50. This directory managing unit 50 is arranged by a LAN interface unit 50A, a command interface unit 50B, a command processing unit 50C, a directory retrieving/processing unit 50D, a directory filing/processing unit 50E and a directory data unit 50F.

FIG. 4B represents an internal arrangement of the first database unit 20. Since the first database unit 20 has the same arrangement of the respective remaining database units 22 and 24, only first database unit 20 will now be explained. The first database unit 20 is constructed of a LAN interface unit 60A, a command interface unit 60B, a command processing unit 60C, a database retrieving/processing unit 60D, a database filing/processing unit 60E and a database data unit 60F.

FIRST IMAGE DATA RETRIEVING METHOD

A first method for retrieving image data performed in the above-described first image data retrieving system 100 will now be described with reference also to three flowcharts shown in FIGS. 5, 6 and 7.

It should be noted that the first image data retrieving method is performed in the first system 100, as shown in FIG. 1, that the directory managing unit 50 is independently employed with respect to the database units 20-24 and the workstations 30-32.

Figure 5:
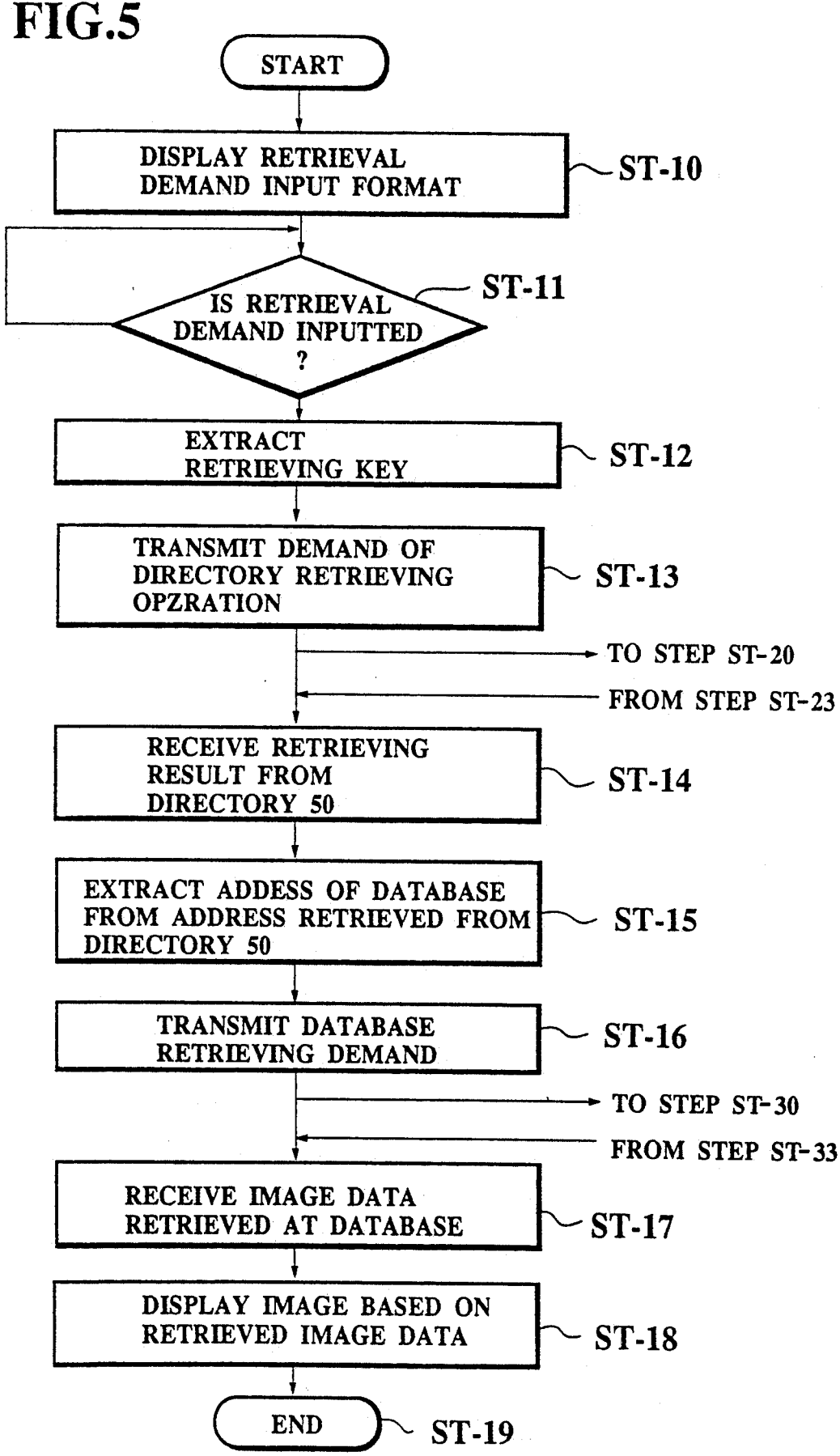

FIG. 5 is a flowchart for explaining the image data retrieving operation effected at the workstation, FIG. 6 is a flowchart for explaining the retrieving operation executed at the directory managing unit 50, and FIG. 7 is a flowchart for explaining the retrieving operation performed at the database unit.

In the image data retrieving operation performed at the workstation 30 or 32 as represented in FIG. 5, an image data retrieval demand input format is displayed at a first step ST-10. Then, a check is made whether or not the image data retrieval demand has been inputted at a next step ST-11. If YES, then the retrieving process is advanced to a step ST-12 at which a retrieving key is extracted thereafter, a demand for executing the directory retrieving operation is transmitted via LAN 40 to the directory managing unit 50 at a step ST-13.

Accordingly, the process is advanced to the retrieving operation at the directory managing unit 50. At a first step ST-20 of FIG. 6, the demand for performing the directory retrieving operation is received. Then, a retrieving key is extracted from the demand at a step ST-21. As a result, an address of the image data is retrieved at this directory retrieving unit 50 at a step ST-22, and thus the retrieved address is sent to the workstation(at a step ST-14 of FIG. 5).

Returning to the main flowchart of FIG. 5, an address of the relevant database unit 20-24 corresponding to the retrieved address of the directory managing unit 50 is picked up therefrom at a step ST-15. At the subsequent step ST-16, another retrieving demand is sent from the workstation 30 or 32 to the relevant database unit 20-24.

At a first step ST-30 of the retrieving operation shown in the flowchart of FIG. 7, this database retrieving demand is retrieved. Thereafter, a retrieving key is extracted from the database retrieving demand at a step ST 31. Then, the desired image data is retrieved from the relevant database 20-24 based upon this retrieving key at a step ST-32, and this retrieved image data is sent to the workstation (at a step ST-17 of FIG. 5).

Consequently, workstation displays the desired medical image data sent from the relevant database unit at a step ST-18. As previously stated the above-described first image data retrieving operation is accomplished at a step ST-19 of FIG. 5.

This first image data retrieving operation will now be summarized. Assuming now that the directory managing unit 50 manages such a directory of the directory file shown in FIG. 2, and also the medical image related to the patient No. 01, patient name of "SATO" and examination date of 91-2-14 is to be retrieved at the first workstation 30, these examination data are inputted in this workstation 30 and transferred to the directory managing unit 50. In this directory managing unit 50, the directory file shown in FIG. 2 is retrieved and then the logic address such as DB "No. 1" and address of "1" is obtained. Thereafter, the retrieved logic address is returned to the workstation 30 which will demand the first database unit 20 to obtain the medical image stored at the address of "1". Accordingly, this database unit 20 retrieves this image data at the address of "1" and returns the retrieved image data to the workstation 20.

It should be noted that since the above-described first image data retrieving operations as described in the detailed flowchart operations of FIGS. 5 to 7 are executed in the respective internal units of the workstation 30 shown in FIG. 3 and of the directory managing unit 50 shown in FIG. 4A and also of the database units 20 of FIG., 4B to 24, no further explaining thereof is made in the specification.

SECOND IMAGE DATA RETRIEVING METHOD

A second image data retrieving method of the present invention will now be described which is, in principle, performed in the retrieving system 100 shown in FIG. 1. However, the internal arrangements of the workstation 34 and also of directory managing unit 52 employed to execute this second retrieving method are different from those for the first retrieving method, which are newly employed instead of the workstations 30, 32 and directory managing unit 50.

Figure 8:
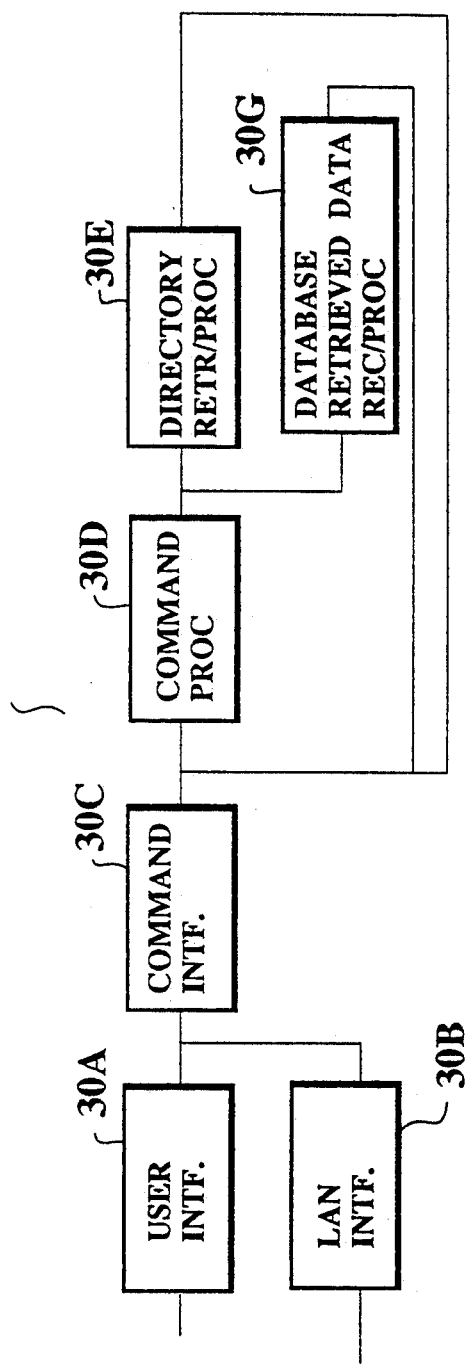
FIG. 8 is a schematic block diagram for representing an internal arrangement of the workstation 34.
Figure 9:
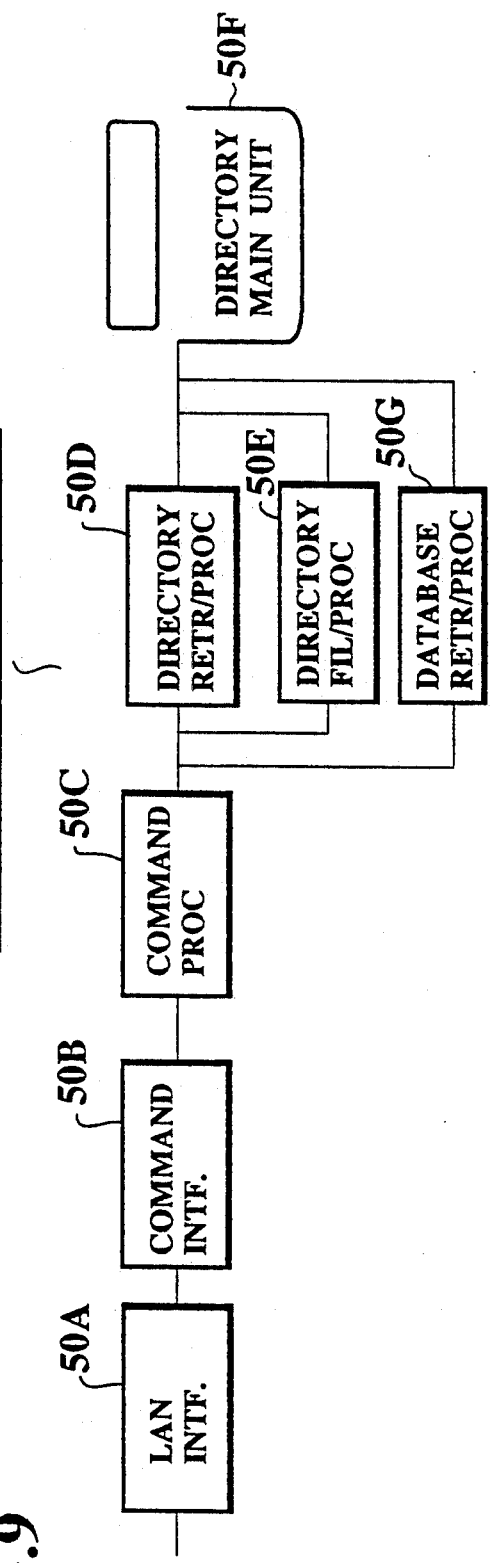
FIG. 9 is a schematic block diagram for representing an internal arrangement of the directory managing unit 52.

This is, FIG. 8 is a schematic block diagram for showing the internal arrangement of the workstation 34 and FIG. 9 is a block diagram for representing the internal arrangement of the directory managing unit 52. The same reference numerals shown in FIG. 3 and 4 will be employed as these for denoting the same or similar circuit units in the following drawings.

A major feature of the second medical image data retrieving method is such that desired image data stored in the relevant database units 20–24 is requested by the directory managing unit 52 to be transferred to the workstation 34.

Figure 10:
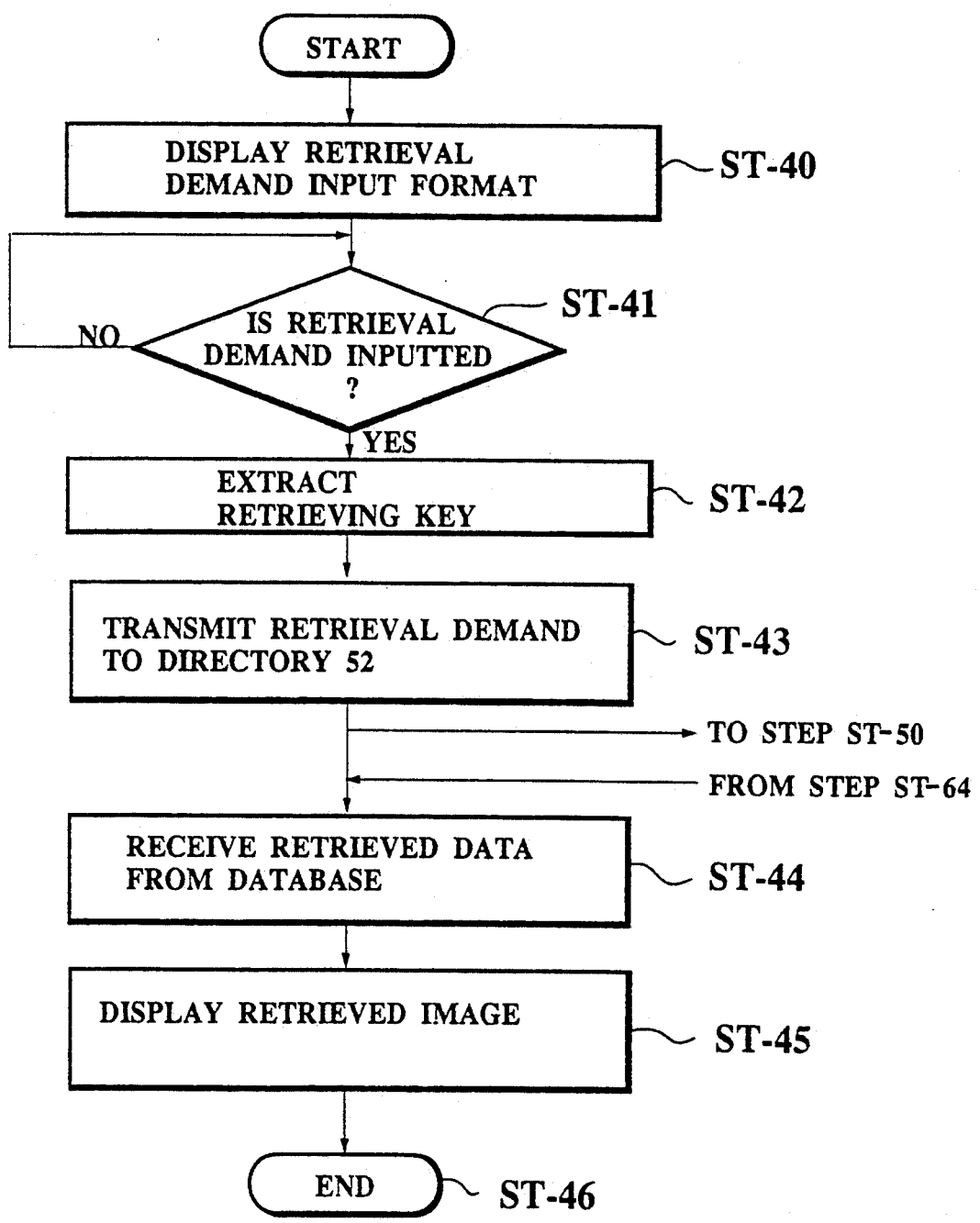
FIGS. 10 to 12 are flowcharts for representing a second image data retrieving operation performed in the system 100.
Figure 11:
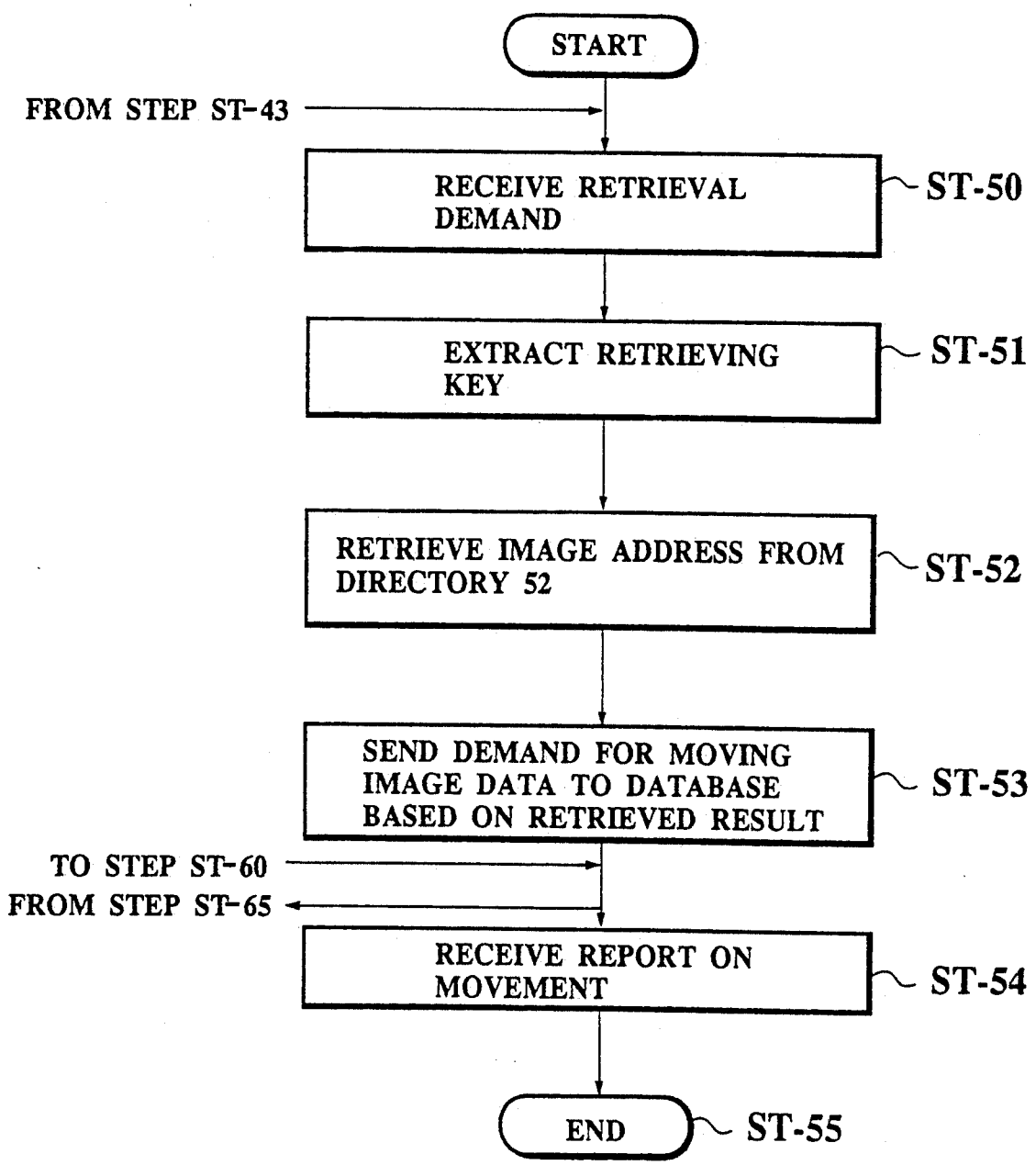
Figure 12:
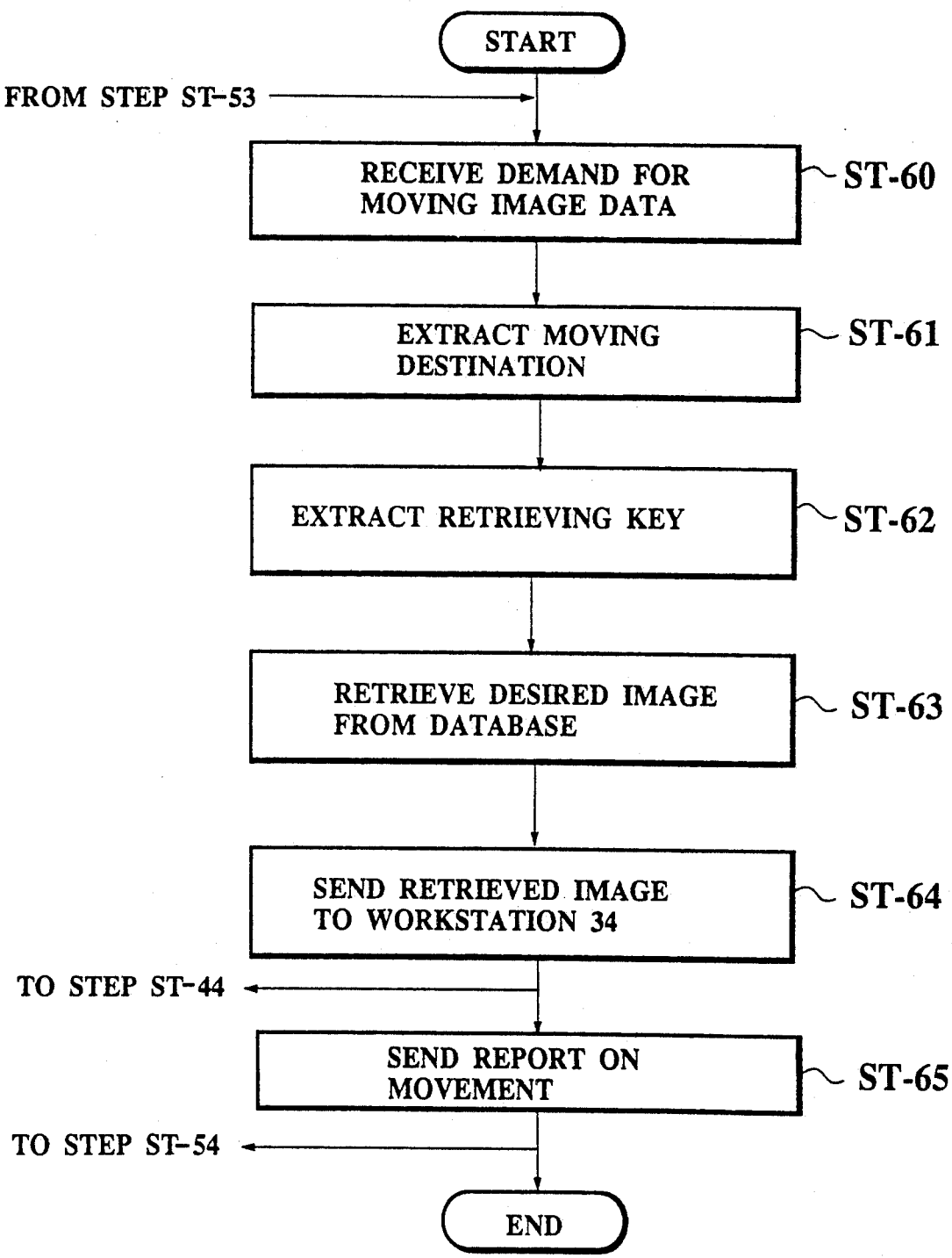

FIG. 10 is a flowchart for showing an image data retrieving operation effected in the workstation 34 of FIG. 8, FIG. 11 is a flowchart for showing an image data retrieving operation performed in the directory managing unit of FIG. 9, and also FIG. 12 is a flowchart for representing an image data retrieving operation carried out in the database unit 20–24.

In the main flowchart shown in FIG. 10, since the retrieving process steps from ST-40 to ST-43 are the same as in the main flowchart of FIG. 5, explanations thereof are omitted. At the step ST-43, the workstation 34 shown in FIG. 8 sends the image data retrieval demand to the directory managing unit 52 shown in FIG. 9. Thus, an address of the desired image data stored in the directory managing units 52 is retrieved in accordance with the process steps ST-50 to ST-52 as defined the flowchart of FIG. 11. Subsequently, the directory managing unit 52 shown in FIG. 9 transmits a demand for moving the image data of the directory managing unit 52 to the relevant database unit 20–24 at a step ST-53.

In response to this demand from the directory managing unit 52, the relevant database unit 20–24 starts to retrieve the desired medical image data from this database in accordance with the retrieving processes as defined at the steps ST-60 to ST-63. At the next step ST-64, the retrieved image data is transferred from this database unit to the workstation 34, and then this database unit sends a report on a completion of image movement to a step ST-54 of FIG. 11. Upon receipt of this report, the directory managing unit 52 accomplish the image data retrieving operation thereof at a step 55. On the other hand, the workstation 34 receives the retrieved image data from the relevant database unit and displays the desired medical image based on the received image data at a step ST-44 and finally the second retrieving operation is ended at a step ST-45.

The above-described second image data retrieving operation will now be summarized under such conditions that the directory file as shown in FIG. 2. In case that a medical image of such examination states: patient No. 1; name of patient "SATO" and examination date of 91'-02-14 is retrieved at the workstation 34 shown in FIG. 8, this workstation 34 sends the above examination data to the directory managing unit 52 shown in FIG. 9. In response to these data, the directory file is retrieved so as to obtain the logical address of DB-No. 1 and address of "01", and the directory managing unit 52 sends to the first database 30 the demand for moving of "01" toward the workstation 34. Then, the first database unit 30 retrieves the image data at the address of "01" and thereafter sends the retrieved image data to the workstation 34 and also reports that the image movement has been accomplished to the directory managing unit 52.

THIRD IMAGE DATA RETRIEVING METHOD

A third image data retrieving method according to the present invention has such a particular feature that both of the above-described first and second image data retrieving methods are combined with each other and one of these retrieving method is properly selected based upon a selecting basis, for instance, a capacity of a disk. This third image data retrieving method may be executed in the retrieving system shown in FIG. 1, in which a workstation 36 as shown in FIG. 13 is newly employed instead of the workstations 30–34 shown in FIG. 3 and 8, and workstations 30–34 shown in FIG. 3 and 8, and the same directory managing unit 52 shown in FIG. 9 and the same database units 20–24 shown in FIG. 4B are employed.

Figure 13:
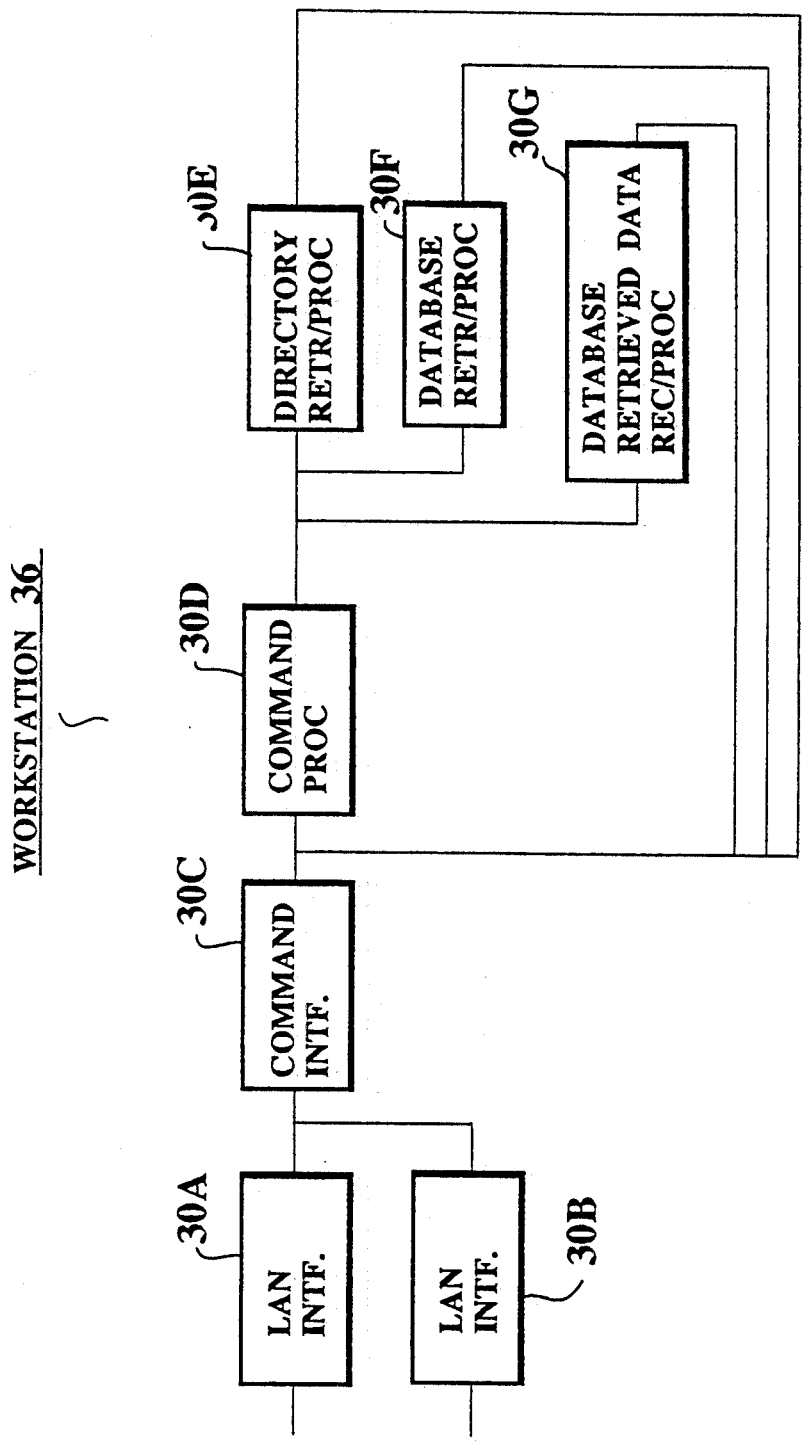
FIG. 13 is a schematic block diagram for representing an internal arrangement of the workstation 36.
Figure 14:
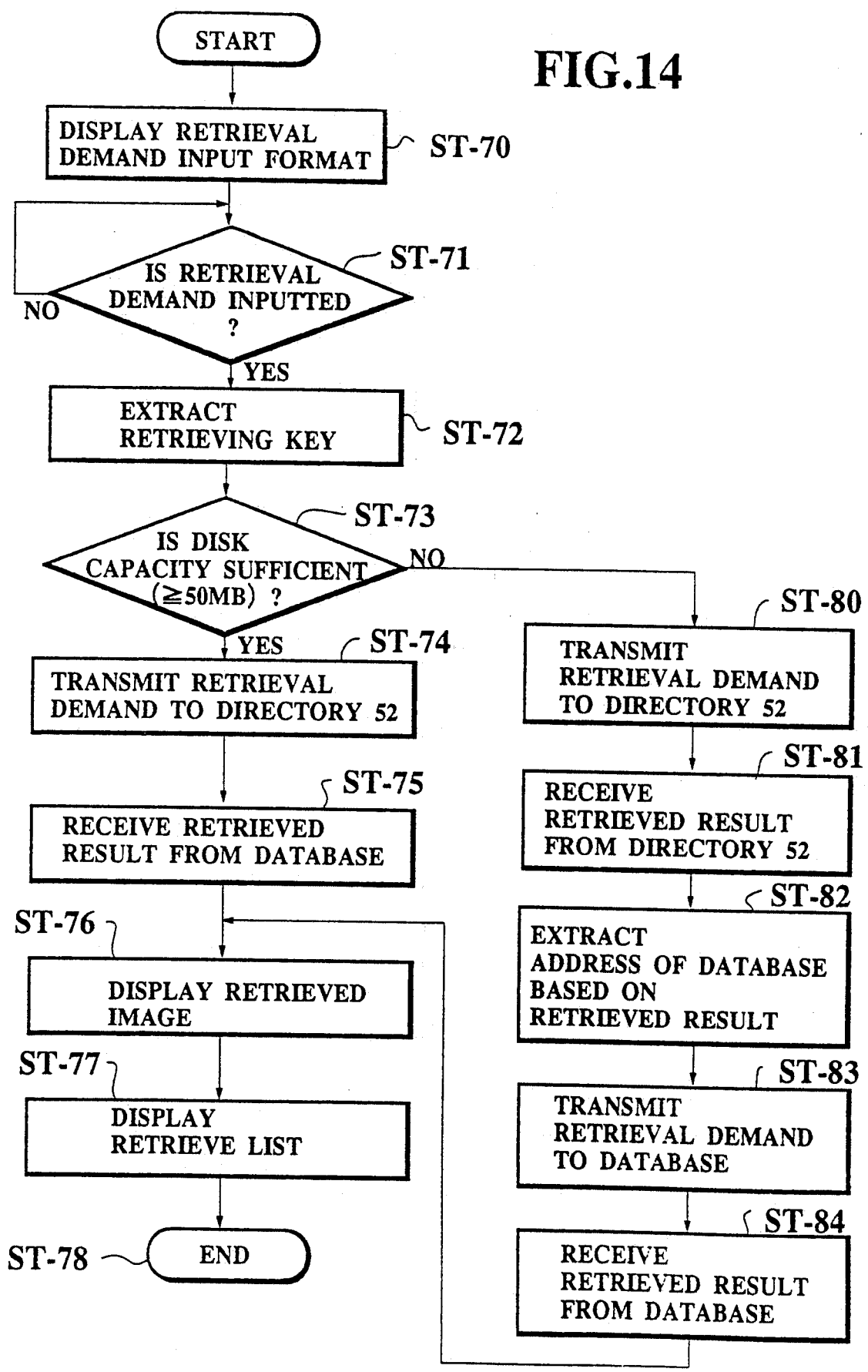
FIGS. 14 and 15 are flowcharts for explaining a third image data retrieving method executed in the system 100.
Figure 15:
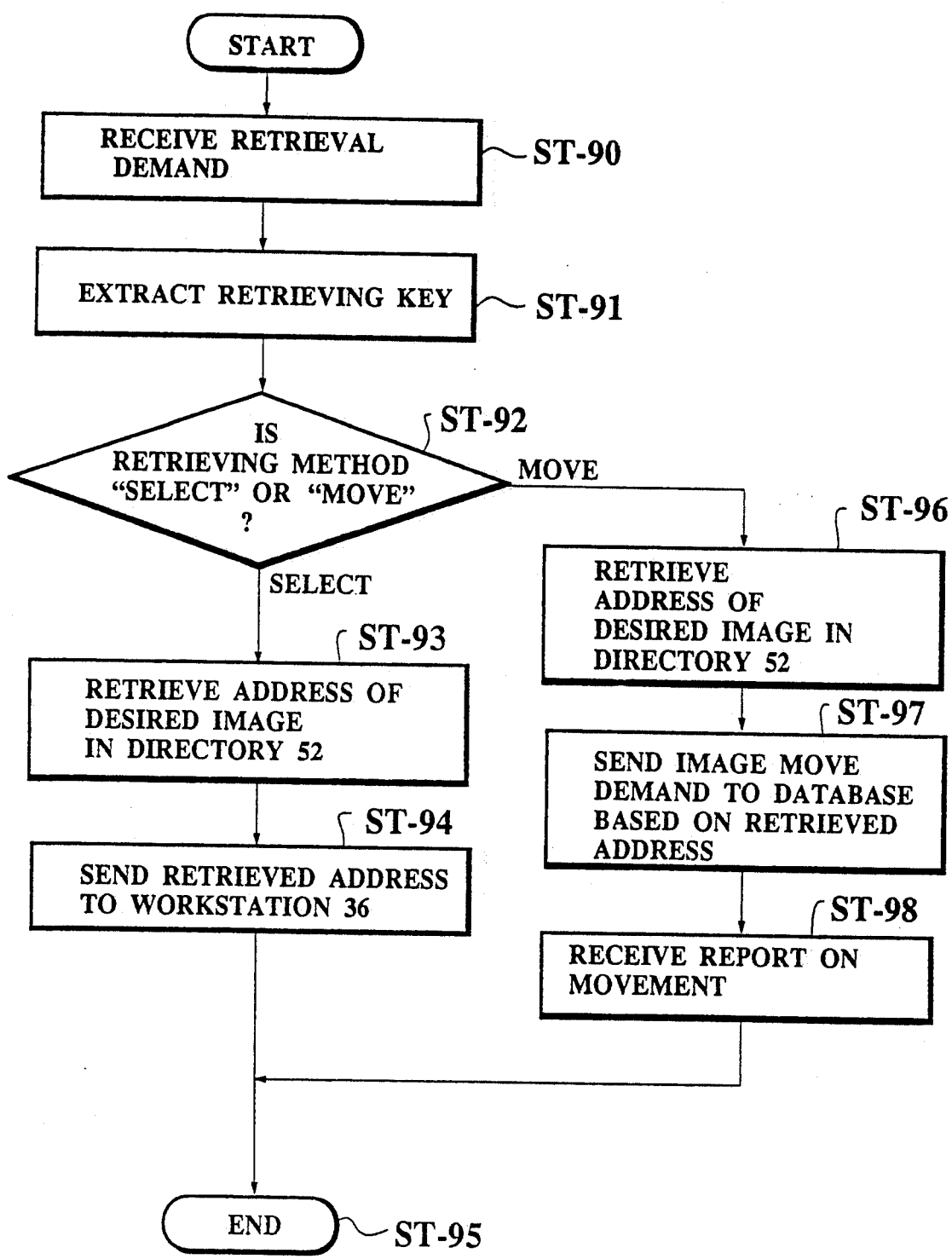

FIG. 14 is a flowchart for explaining an image data retrieving operation effected at the workstation 36 of FIG. 13, and FIG. 15 is a flowchart for explaining an image data retrieving operation performed at the directory managing unit 52 of FIG. 9.

In the third retrieving method as defined in FIG. 14, the same process as described in, for instance, the steps from ST-10 to ST-12 of FIG. 5 is executed. Thereafter, a judgment is made at a step ST-73 whether or not a capacity of a disk employed in the workstation 36 is sufficient (will be discussed later). If YES, then a step ST-74 is performed, that is, the retrieval demand is transmitted from this workstation 36 to the directory managing unit 52. Subsequently, the retrieved result is received from the relevant database units 20–24 at a step ST-75 and the retrieved image is displayed at a next step ST-76. Then, a retrieve list is displayed at a step ST-77 and this third retrieving method is ended at a step ST-78.

If "NO" at the previous step ST 73, then the process is advanced to another step ST-80 at which a retrieval demand is sent from this workstation 36 to the directory managing unit 52. At the subsequent step 81, the retrieved result is received from this directory managing unit 52. Then, an address of the relevant database unit 20-24 is directory managing unit 52 at a step AT-82. A further retrieval demand is sent to the relevant database unit at a next step ST-83 and then the retrieved result of this database unit is received at a step ST-84. Thereafter, the process is advanced to the previous step ST-76.

Now, the retrieving operation performed at this directory managing unit 52 will be described more in detail with reference the flowchart shown in FIG. 15.

In this flowchart, the retrieval demand is received at a step ST-90 and then the retrieving key is extracted from this demand at a step ST-91. At a next step ST-92, a check is made whether the retrieving method is "SELECT" or "MOVE". If the "SELECT" method is selected, then the process is advanced to a step ST-93 where an address of the desired image data is retrieved in the directory managing unit 52. Subsequently, the retrieved address is sent to the workstation 36 at a step ST-94 and this retrieving method is accomplished at a step ST-95.

If the "MOVE" method is selected at the previous step-92, then the address of the desired image data is retrieved in the directory managing unit 52 at a step ST-96. At a next step ST-97, a demand for moving the image data is sent to the relevant database unit 20-24 based upon the retrieved address and further, an announcement that the image movement has been accomplished is received from the database unit at a next step ST-98. As a result, this retrieving operation is ended at the step ST-95.

The above-described third data retrieving operation will now be summarized.

It is assumed that the directory is shown as a directory file of FIG. 16. When all of medical images relating to one patient, for instance, ID No. P00001 are wanted to be retrieved at the workstation 36, the capacity of the disk (not shown in detail) employed in this workstation 36 is investigated. If there is sufficient empty in the disk capacity, the move retrieving method (i.e., the second retrieving method as shown in FIG. 10) is executed. To the contrary, if the disk capacity is not sufficient, the SELECT retrieving method (i.e., the first retrieving method as shown in FIG. 5) is performed. This judgment basis is determined by, for instance, an average amount of stored images for a single patient. In this preferred embodiment, this average value is selected to be 50 MB. Assuming now that the empty capacity of the disk employed in the workstation is 20 MB, a judgment is made by this workstation that the capacity of the disk is not sufficient and therefore, the SELECT (first) retrieving method is performed. In this SELECT retrieving method, since the directory managing unit 52 retrieves from the directory file the examination ID, the name of database, and the image volume or size of this examination and sends these file data to the workstation, the workstation investigates this image volume or size in order that the capacity storable therein is calculated, and also determines an examination for retrieving the image. In this preferred embodiment, such a rule is determined that the priority of the first examination becomes higher than that of the subsequent examination, when the examinations are determined. It should be noted that the numbers of the examination IDs indicate old or new. When the workstation investigates the first examination "E00210", the image volume or size of this examination is 18 MB and the image volume or size of the subsequent examination "E00143" is 5 MB, so that it can be judged that only the first examination :"E00210" may be stored within the present empty capacity of 20 MB in the workstation. As a consequence, this workstation sends to the relevant database unit such a retrieval demand that the medical image data of the examination No. "E00210", and then receives such a demanded image data from this database unit so as to be displayed. Simultaneously, this workstation also displays a mark by which a user may recognize that the desired image data is not yet retrieved.

FORTH IMAGE DATA RETRIEVING METHOD

A forth image data retrieving method according to the present invention will now be described. A feature of the forth retrieving method is as follows. Each of database units owns a directory of data which have been previously stored in its database unit, for instance, a surgery directory file shown in FIG. 17, an internal medicine directory file shown in FIG. 18, and an obstetrics directory file shown in FIG. 19. Furthermore, a directory managing unit owns such a directory file as represented in FIG. 2.

Assuming now that the firstly retrieved database unit is predetermined, depending upon the selected workstation, the forth retrieving operation is carried out as follows.

For instance, when the first workstation 30 firstly issues interrogation to the surgery directory file shown in FIG. 17 stored in the first database unit 20, if the desirable image data, e.g., the name of diagnosis and storage address are retrieved from this database unit 20, these image data are transferred to the first workstation 30 and the retrieving method is accomplished. To the contrary, if there is no desired image data in this surgery directory file, then the following retrieving operation will be executed as represented in a flowchart of FIGS. 20A and 20B.

Figure 20A:
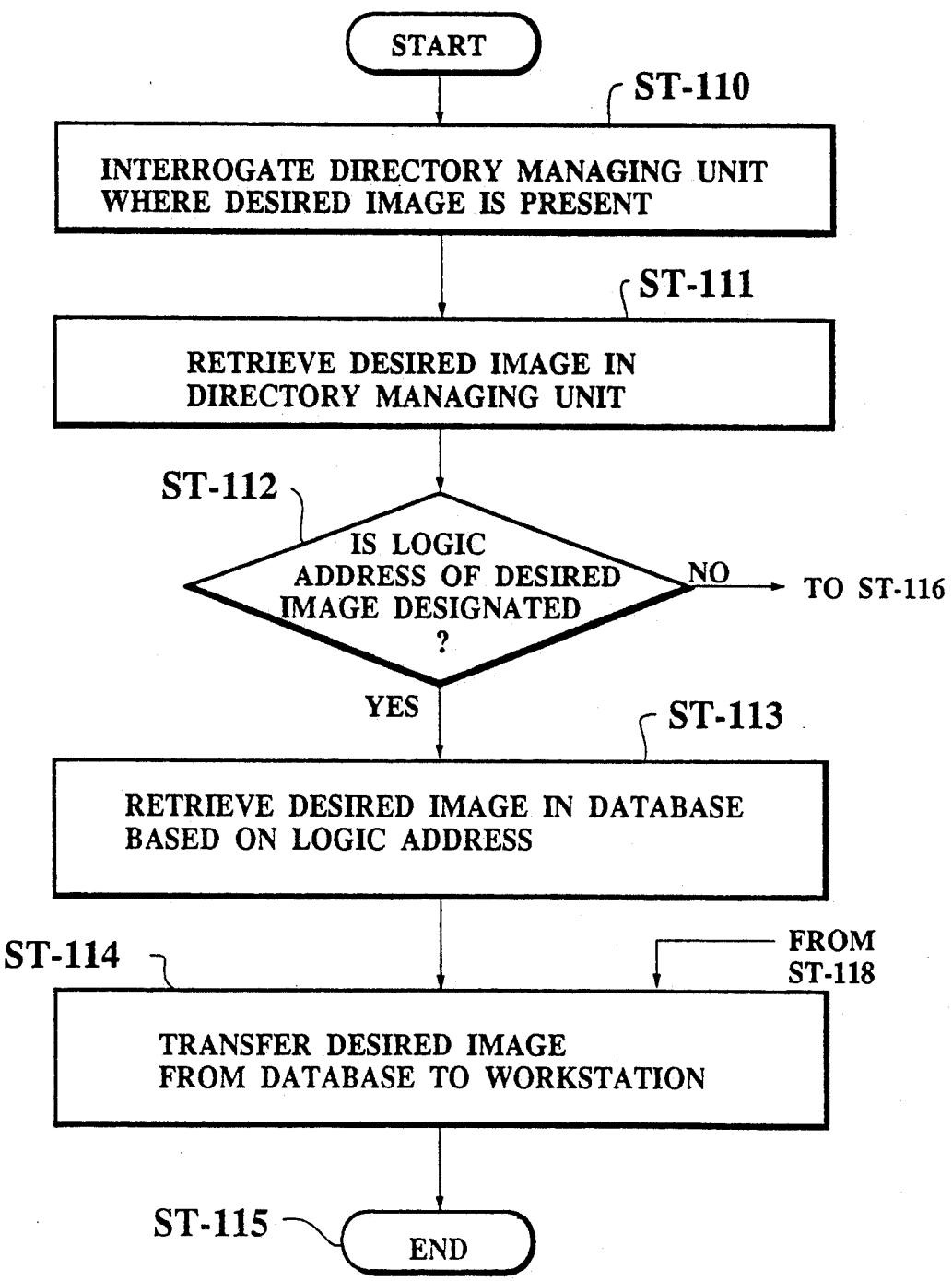
FIGS. 20A and 20B re flowcharts for representing a fourth image data retrieving method.
Figure 20B:
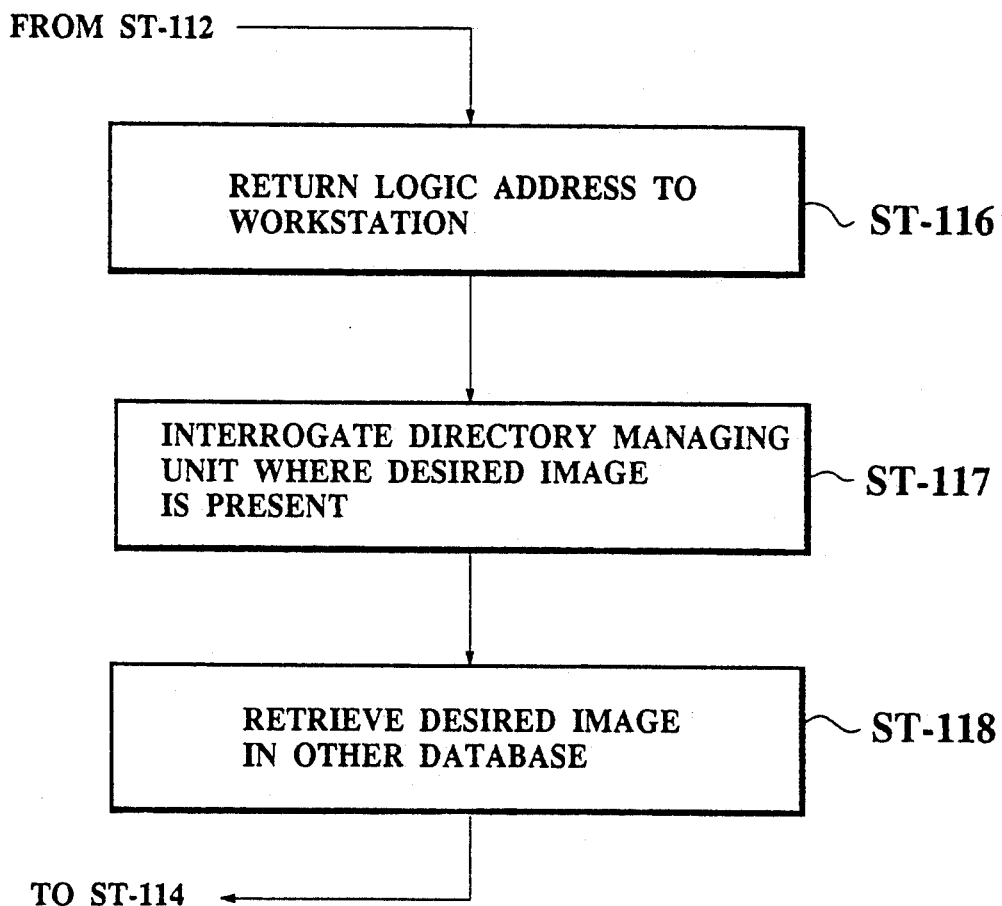

In the flowchart of FIG. 20A, the first workstation 30 issues such an interrogation where the desired image data is present, to the directory managing unit 50 which previously stores such a concentrated directory file as indicated in FIG. 2 at a step ST-110. Thereafter, the directory managing unit 50 retrieves the desired image data in the own directory file at a step ST-111. At a next step ST-112, a check is made whether or not a logic address indicative of the desired image data is designated. If "YES", then the process is advanced to a further step ST-113 at which the desired image data is retrieved in the relevant database unit 20-24 based on the logic address. Subsequently, the retrieved image data is transferred from this database unit to the first workstation 30 at a step ST-114. Thus, this fourth retrieving method is completed at a step ST-115.

At the judging step ST-112, if the judgment result becomes "NO (no designation)", then the process is advanced to a step ST-116 at which this logic address is retrieved to the first workstation 30. Then, this workstation 30 interrogates the directory managing unit 50 where the desired image data is present based on this logic address at a step ST-117. Accordingly, the desired image data is retrieved in the relevant database unit other than the first-mentioned database unit at a step ST-118. Finally, the desired image data is transferred from this database unit to the first workstation at the step ST-114, and this retrieving method is ended at the step ST-115.

MEDICAL IMAGE DATA FILING SYSTEM

Figures 21, 22:
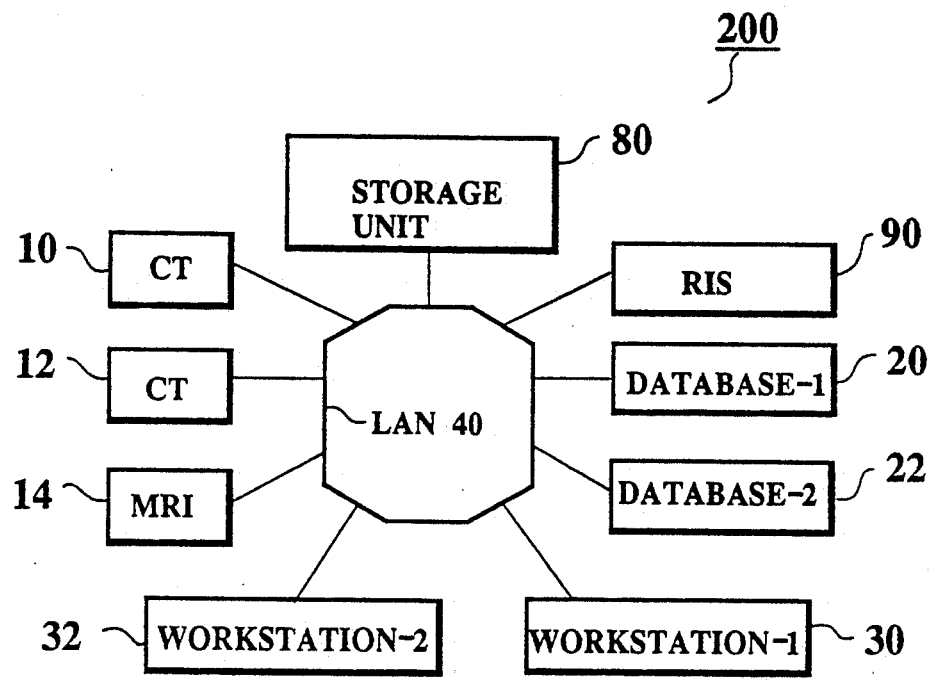
FIG. 21 is a schematic block diagram for showing an overall arrangement of an image data filing system 200 according to the present invention.
FIG. 22 represents a content of a filing destination information file stored in the storage unit 80 employed in the system 200 shown in FIG. 21.

Referring now to FIG. 21, a basic arrangement of a medical image data filing system 200 accordingly to the present invention will be described. This filing system 200 similarly comprises the modalities 10-14; the database units 20-22; and the workstations 30-32. The filing system 200 further comprises a storage unit 80 and RIS (radiology information system) 90. The storage unit 80 stores, for instance, such a file of filing destination data or information as represented in FIG. 22. It should be noted that this storage unit 80 may be realized by the directory managing unit 50 shown in FIG. 1. The radiology information system 90 may provide medical data on radiology.

In the medical image data filing system 200, it is assumed that the storage unit 80 stores filing destination information as shown in FIG. 26. When an X-ray CT examination is carried out, the CT apparatus 10 as the modality fetches various medical data required for retrieving the filing destination information, for instance, the patient ID "P00001" and the examination ID "E00105", and then transfers these medical data to the storage unit 80. In this storage unit 80, the examination ID functioning as the key word is extracted from the transferred data and this extracted key word is sent to the radiology information system (RIS) 90 in order to retrieve the name of examination from RIS 90, necessary for retrieving the filing destination information. Upon receipt of this examination ID, RIS 90 retrieves which examination department has requested such an examination. In this case, the inter medicine department has dispatches such a request. Accordingly, the retrieved result "internal medicine" is sent from RIS 90 to the storage unit 80. Subsequently, the storage unit 80 retrieves the filing destination information based on this retrieved result "inter medicine". Then, the resultant filing destination information "filing apparatus A" is transferred to the CT apparatus 10, and then this CT apparatus 10 sends the examination data produced therein to the filing apparatus A (i.e., database unit 20).

Figure 23:
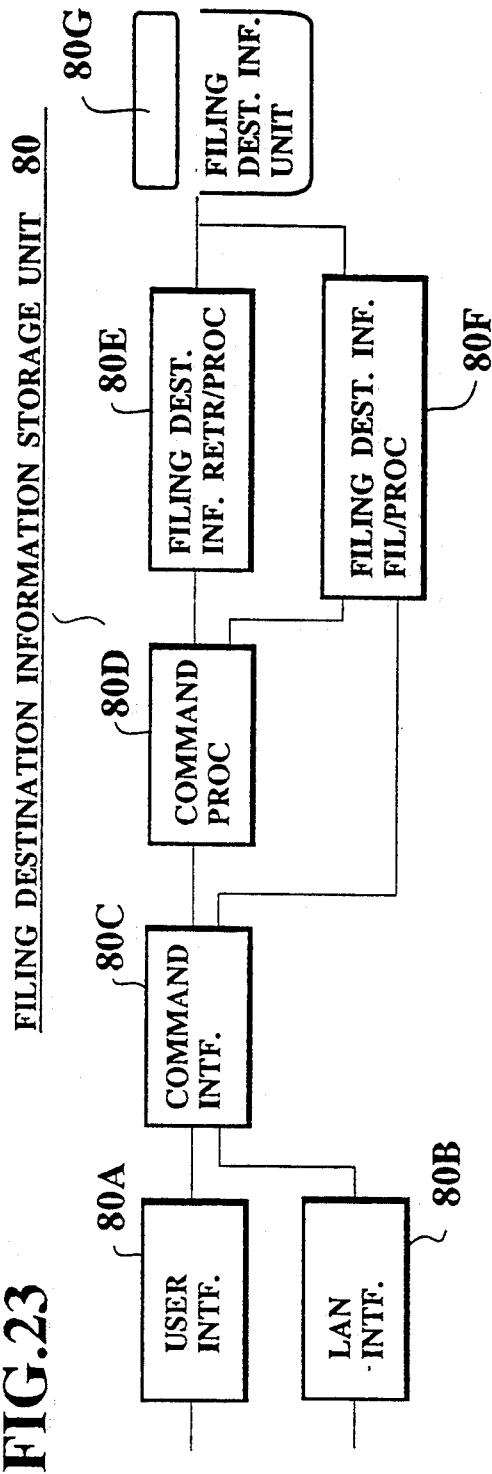
FIG. 23 is a schematic block diagram for showing an internal arrangement of the filing destination information storage unit 80.
Figure 24:
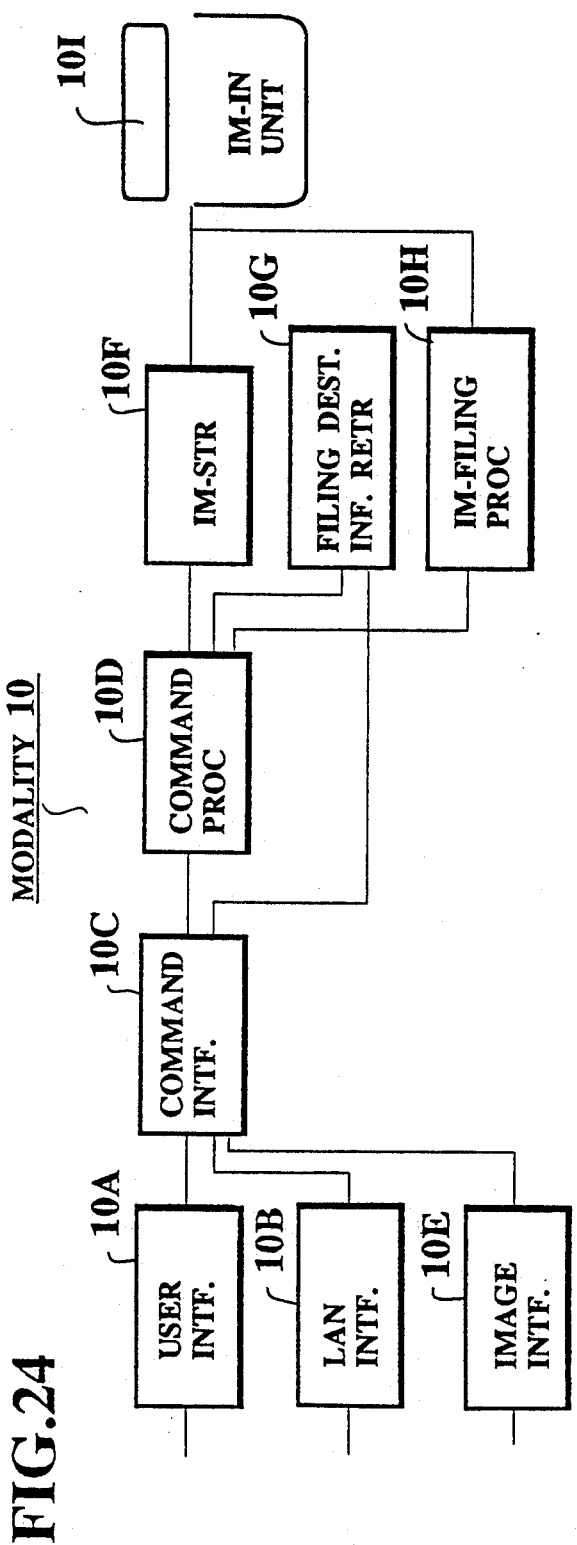
FIG. 24 is a schematic block diagram for representing an internal arrangement of the modality 10.

An internal (logic) arrangement of the filing destination information storage unit 80 is shown in FIG. 23 and an internal arrangement of the respective modalities 10-14 is represented in FIG. 24. The filing destination information storage unit 80A, a LAN interface unit 80B, a command interface unit 80C, and a command processing unit 80D, which are similar to those of other units, e.g., the directory managing unit 50 of FIG. 4A. Furthermore, a filing destination information retrieving/processing unit 80E, a filing destination information filing/processing unit 80F and a filing destination information unit 80G, the detailed operations of which will be described later. The modality 10 shown in FIG. 24 has common circuit elements as those of the remaining modalities 12 and 14. The modality 10 comprises a user interface unit 10A, a LAN interface unit 10B, a command interface unit 10C, a command process unit 10D and an image input interface unit 10E, and further an image storage process unit 10F, a filing destination information retrieving unit 10G, an information filing process unit 10H and an image information unit 101, the detailed operations of which will be also described later.

Referring now to flowcharts of FIG. 25A and 25B, a medical image data filing method according to the present invention will be described, which is performed in the filing system 200 of FIG. 21.

Figure 25A:
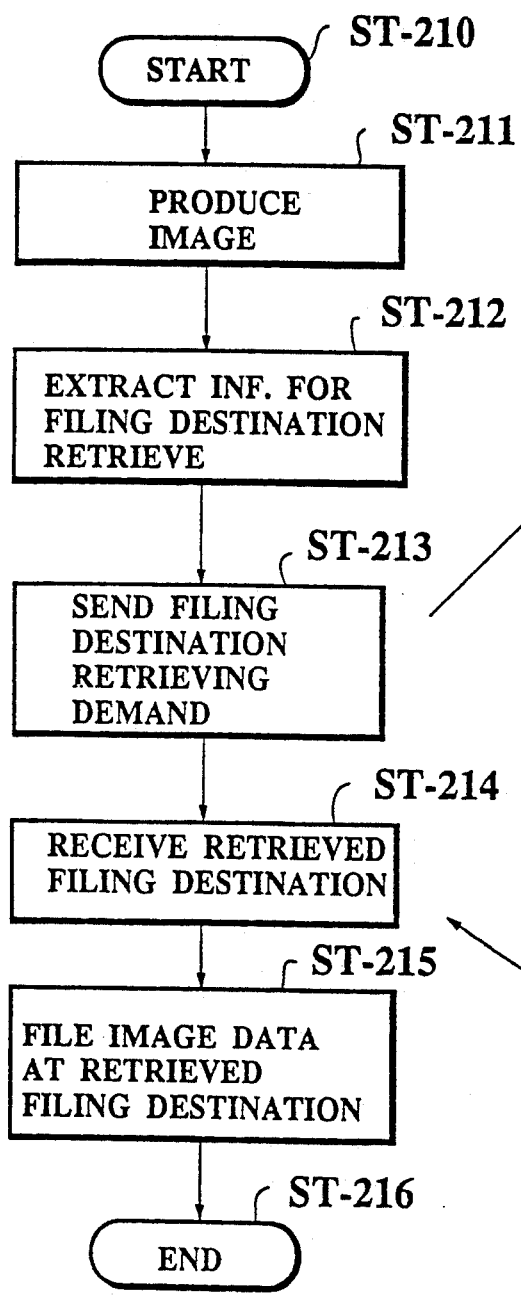
FIGS. 25A and 25B are flowcharts for explaining a first data filing operation effected in the system 200.
Figure 25B:
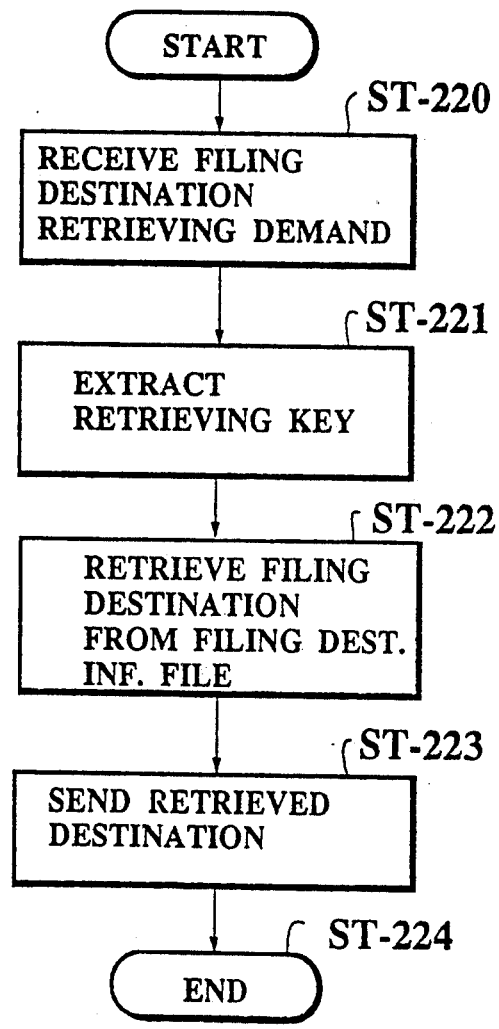

The first flowchart of FIG. 25A represents a filing operation effected in the modality 10 of FIG. 24, whereas the second flowchart of FIG. 25B indicates a data retrieving operation performed in the storage unit 80.

In the modality filing operation, the operation starts at a first step ST-210, and a medical image related to this modality 10 is generated at step ST-211. At a next step ST-212, information required for retrieving filing destination information is extracted. Thereafter, the modality 10 sends to storage unit 80 a demand for retrieving the filing destination at a step ST-213. As a result, this demand is received at the storage unit 80 at a step ST-220 of the flowchart shown in FIG. 25B. Then, a retrieving key is extracted at a step ST-221, and the filing destination is retrieved from the filing destination information file at a next step ST-222. Thus, this retrieved destination is sent to the modality 10 at a step ST-223. In the modality 10, the retrieved destination is received from the storage unit 80 at a step ST-214. Accordingly, the medical image data is filed at this retrieved destination at a step ST-215 and this filing operation is completed at a step ST-215.

It is assumed that a filing destination file as shown in FIG. 26 has been stored in the storage unit 80, and a certain examination at the first modality 10, i.e., CT-1 is carried out. This CT apparatus 10 extracts the information required for retrieving the filing destination information, such as the patient ID number "P00001"; the examination ID "E00105"; the diagnosis "INTERNAL MEDICINE"; the name of modality "CT"; and the examination apparatus ID "M014", and then transfers these information to the storage unit 80. In the storage unit 80, the retrieving key, namely "INTERNAL MEDICINE" is extracted from these information so as to retrieve the filing destination information. In this case, since "the filing apparatus A" corresponds to this filing destination information, "the filing apparatus A" is sent to the CT apparatus 10. Then, the CT apparatus 10 transfers the produced examination results to the filing apparatus A.

The filing destination information file employed in this preferred embodiment is used under such operation to determine to which database, the medical image data belonging to the relevant diagnostic department is filed. This filing destination information file may be formed by inputting the data an operator (user).

FORMATION OF FILING DESTINATION INFORMATION FILE

A formation of such a filing destination information file will now be described.

While observing an input screen shown in FIG. 27A, both a basis to categorize the database units 10-14 and a basis to judge the sequence are inputted by a user or operator. The medical image data acquired by the MRI apparatus 14 are entered into one database unit. If these MRI data are wanted to be categorized in unit of the diagnostic department, "1" is inputted to the judging sequence of the name of the examination apparatus and also "2" is inputted to the judging sequence of the diagnostic department. Upon completion of input operation, since the input screens of the relationships in accordance with the respective bases are displayed as shown in FIG. 27B and 27C in the order of the judging sequence, the operator enters necessary data while observing these input screens. When all of the above-described input operations are completed, a confirmation screen as shown in FIG. 27D is displayed. If the contents of this confirmation screen are in satisfactory conditions, a filing destination information file as indicated in FIG. 28 is formed.

It should be noted that since the retrieving method has been established within the storage unit 80 in case that the basis to categorize the database units is employed, this retrieving method is executed in accordance with the sequence of the inputted priority order.

A flowchart of FIG. 29 briefly represents the above-described forming operation of the filing destination information file.

As apparent from this flowchart, the filing operations defined from the step ST-230 to the step ST-236 have been described above. At the subsequent step ST-237, the input data are converted into the corresponding table for the storage purpose. Thereafter, a decision is made of the sequence for retrieving the filing destination information. Thus, the formation of the filing destination information file is accomplished at a step ST-239.

MODIFICATIONS OF FILING DESTINATION INFORMATION

When the filing destination information is modified, new filing destination information may be simply filed in accordance with the same filing method as described above. This is a particular feature of this image data filing system of this image data filing system according to the present invention that since the sequences of the retrieving operation with respect to the filing destination information table the filing destination information are changed when the new filing destination information is newly filed, the filing destinations of the image data acquired in the modalities 10-14 may be changed without any filing modification by merely modifying the contents of the filing destination information storage unit 80.

Figure 30A:
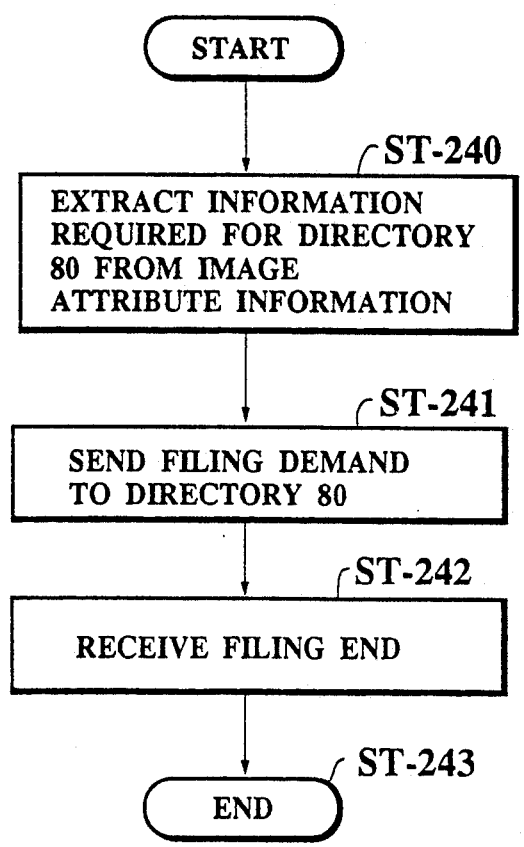
FIGS. 30A and 30B are flowcharts for explaining a second directory filing operation effected in the system 200.
Figure 30B:
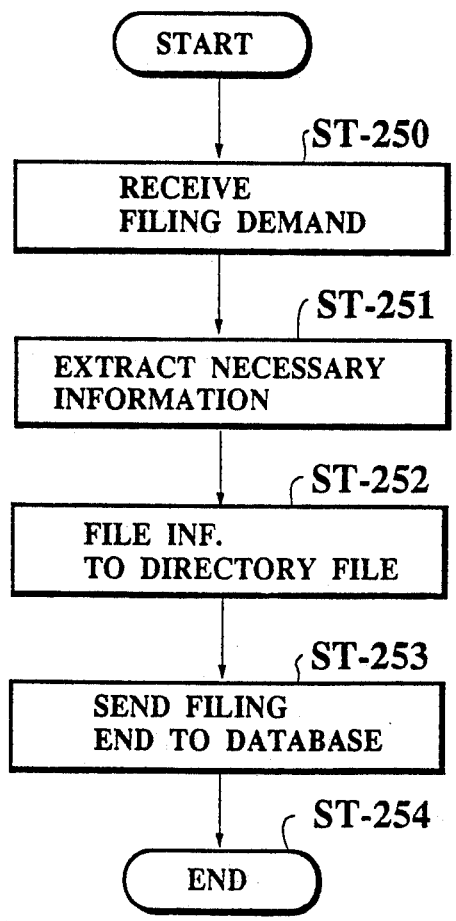

Subsequently, filing operation for the directory managing unit 80 and the database 10-14 will now be explained with reference to FIGS. 30A and 30B under such conditions that filing destinations of image data are recognized in the respective modalities 10-14, and the image data together with the attribute information such as the patient ID numbers have been filed in the relevant database unit. FIG. 30A is a flowchart for explaining the directory filing operation effected in the database, and FIG. 30B is another flowchart for explaining the directory filing operation performed in the directory managing unit.

In the directory filing operation executed in the database unit 10-14 as shown in FIG. 30A, information required for forming directory file in the directory managing unit 80 is extracted from the image attribute information at a first step ST-240. A filing demand is sent to the directory managing unit 80 at a step ST-241. As a result, this filing demand is required by the directory managing unit 80 at a step ST-250 as shown in the flowchart for representing the filing operation executed in the directory managing unit 80 of FIG. 30B. At the next step ST-251, necessary information is extracted. Then, this information is filed in the directory file at a step ST-252 and a filing completion report is transmitted from the directory managing unit 80 to the database unit 10-14. Upon receipt of this filing completion report (step 242), the directory filing operation at the database unit is ended at a step ST-243 and also the directory filing operation at the directory managing unit 80 is accomplished at a step ST-254.

Another filing operation for the directory managing unit and the database unit will now be explained under conditions that the filing destinations of the image data are recognized in the modalities and the image data together with the attribute information have been filed in the database units, with reference to FIGS. 31A and 31B. It should be noted that this filing operation is executed in such a case that, as previously described in the retrieving operation, each of the database units 10-14 owns its directory file stored therein and the directory managing unit 80 independently owns all of these directory files.

FIG. 31A is a flowchart for explaining another directory filing operation effected in the database units 10-14 and FIG. 31B is a flowchart for explaining the directory filing operation performed in the directory managing unit 80.

In the flowchart of FIG. 31A, information required for forming a directory file is extracted from the image attribute information at a step ST-2260. At a next step ST-261, the directory file is formed in the database unit. Then, a filing demand of the formed directory file is sent to the directory managing unit 80 at a step ST-262. Since the subsequent operations effected at the directory managing unit 80 are the same as these shown in FIG. 30B, no further explanations thereof are made. At the final step ST-273 of the directory unit 80, the filing end report is similarly transferred to the database unit at a step ST-263 of FIG. 31A. Upon receipt of this filing end reports, the directory filing operation at the database unit is accomplished at a step ST-264.

It should be understood that if the directory file has such a content as shown in FIG. 32, this directory file may be commonly utilized with the filing destination information file. In this case, the directory file information may be inputted in accordance with a method similar to the above-described method for forming the filing destination information, whereas this directory file may be used as the filing destination information file while filing the image data. Also, when the image data are retrieved, it may be readily recognized to which database unit, the interrogation may be issued by referring to this directory file.

What is claimed is:

1. A medical image data managing system, comprising:
    a plurality of modality units, each for producing medical image data in accordance with a type of said each modality unit;
    a plurality of database units, connected to said plurality of modality units, for storing at least said medical image data produced by said modality units, each of said plurality of database units storing a group of related medical image data from said medical image data producing by said modality units;
    directory managing means for storing directory information indicating where the medical image data produced by the modality units is stored in said database units;
    workstation means for issuing a demand, to the directory managing means, to fetch desired medical image data, which corresponds to the demand, from said database units and for displaying the fetched medical image data; and,
    wherein said directory managing means includes at least a first directory managing unit associated with a first of said plurality of database units and a second directory managing unit associated with a second of said plurality of database units, whereby when said demand issued from said workstation means is supplied to one of said first and second directory managing units within the directory managing means and said one directory managing unit determines that the desired image data corresponding to said demand is not contained in said database associated with said one directory unit, said one directory managing unit retrieves the image data corresponding to said demand from the database unit associated with the other of said first and second directory managing units, if said other of said directory managing units contains directory information corresponding to said demand.

2. A medical image data managing system as claimed in claim 1, further comprising:
 a local area network for mutually connecting said modality units, database units, workstation means, and directory managing means so as to establish medical image data communication therebetween.

3. A medical image data managing system as claimed in claim 2, wherein said workstation means includes at least a command process unit for automatically supplying said demand issued therefrom via the local area network to said directory managing means.

4. A medical image data managing system as claimed in claim 1, wherein said directory managing means includes:
 a directory filing/processing unit for instructing said database units to file said produced medical image data produced by said modality units, into said database units; and
 a directory retrieving/processing unit for instructing said database units to retrieve said desired medical image data therefrom thereby to receive said retrieved medical image data.

5. A medical image data managing system as claimed in claim 1, wherein said modality units includes at least one of an X-ray computerized tomographic apparatus, and a magnetic resonance imaging apparatus.

6. A medical image data managing system as claimed in claim 1, wherein said database units each include at least a database retrieving/processing unit, a database filing/processing unit and a database data unit, whereby said medical image data produced by said modality units is filed in said database data units under control of the database retrieving/processing unit thereof and the database filing/processing unit thereof.

* * * * *